(12) United States Patent
O'Hara et al.

(10) Patent No.: US 11,291,508 B2
(45) Date of Patent: Apr. 5, 2022

(54) COMPUTER VISION TECHNIQUES

(71) Applicant: Neuralink Corp., San Francisco, CA (US)

(72) Inventors: Ian M. O'Hara, San Francisco, CA (US); Vikash Gilja, San Diego, CA (US); Kenny Sharma, San Francisco, CA (US); Timothy L. Hanson, San Francisco, CA (US); Timothy J. Gardner, San Francisco, CA (US)

(73) Assignee: NEURALINK, CORP., Fremont, CA (US)

( * ) Notice: Subject to any disclaimer, the term of this patent is extended or adjusted under 35 U.S.C. 154(b) by 0 days.

(21) Appl. No.: 16/569,587

(22) Filed: Sep. 12, 2019

(65) Prior Publication Data

US 2020/0085508 A1 Mar. 19, 2020

Related U.S. Application Data

(60) Provisional application No. 62/731,520, filed on Sep. 14, 2018.

(51) Int. Cl.
*A61B 34/20* (2016.01)
*A61B 34/32* (2016.01)
*A61B 5/00* (2006.01)

(52) U.S. Cl.
CPC ............ *A61B 34/20* (2016.02); *A61B 5/0071* (2013.01); *A61B 5/6848* (2013.01); *A61B 34/32* (2016.02);
(Continued)

(58) Field of Classification Search
CPC ....... A61B 34/20; A61B 34/32; A61B 5/0071; A61B 5/6848; A61B 2034/2055;
(Continued)

(56) References Cited

U.S. PATENT DOCUMENTS

| 6,415,187 B1 | 7/2002 | Kuzma et al. |
| 9,345,389 B2 * | 5/2016 | Nie ........................ A61B 90/37 |

(Continued)

FOREIGN PATENT DOCUMENTS

| JP | 2004307857 A * | 11/2004 |
| WO | 2016126340 A2 | 8/2016 |

(Continued)

OTHER PUBLICATIONS

Translation of JP-2004307857-A (Year: 2004).*
(Continued)

*Primary Examiner* — Serkan Akar
*Assistant Examiner* — Helene Bor
(74) *Attorney, Agent, or Firm* — Kilpatrick Townsend & Stockton LLP

(57) ABSTRACT

Systems and methods that use computer vision techniques in connection with robotic surgery are discussed. A robotic surgery system may include an implantable device engagement sub-system, a targeting sub-system, and/or an insertion verification sub-system. The system may use computer vision techniques to facilitate implanting a micro-manufactured bio-compatible electrode device in biological tissue (e.g., neurological tissue such as the brain) using robotic assemblies. The system can attach, via robotic manipulation, the electrode to an engagement element of an insertion needle. The system can further irradiate the electrode using a near-ultraviolet (near-UV) wavelength of light, obtain images of the electrode with light fluoresced from the polymer portion in response to the irradiating, triangulate a 3D location of the electrode, analyze a target tissue contour using computer vision, select an insertion site, and surgically implant the micron-scale electrode at the insertion site via robotic assembly and based on the triangulated location.

14 Claims, 17 Drawing Sheets

(52) U.S. Cl.
CPC ............... *A61B 2034/2055* (2016.02); *A61B 2034/2065* (2016.02)

(58) Field of Classification Search
CPC ... A61B 2034/2065; A61B 5/24; A61B 5/685; A61B 2562/125; A61N 1/0551; A61N 1/0558
See application file for complete search history.

(56) References Cited

U.S. PATENT DOCUMENTS

| | | | |
|---|---|---|---|
| 9,456,200 B2 * | 9/2016 | Ji | G01C 11/02 |
| 9,782,229 B2 | 10/2017 | Crawford et al. | |
| 2006/0128937 A1 | 6/2006 | Nagasaki et al. | |
| 2008/0027317 A1 * | 1/2008 | Wood | A61B 5/489 600/427 |
| 2010/0100152 A1 * | 4/2010 | Martens | A61B 5/24 607/45 |
| 2010/0168727 A1 | 7/2010 | Hancock et al. | |
| 2013/0010081 A1 * | 1/2013 | Tenney | G05B 19/4086 348/47 |
| 2013/0274596 A1 * | 10/2013 | Azizian | A61B 34/20 600/424 |
| 2013/0345780 A1 | 12/2013 | Tabada et al. | |
| 2014/0277317 A1 | 9/2014 | Tooker et al. | |
| 2014/0303703 A1 | 10/2014 | Mercanzini et al. | |
| 2015/0018622 A1 | 1/2015 | Tesar et al. | |
| 2016/0278678 A1 | 9/2016 | Valdes et al. | |
| 2017/0112354 A1 | 4/2017 | Dicarlo et al. | |
| 2017/0172446 A1 * | 6/2017 | Kuzum | A61B 5/0071 |
| 2018/0014851 A1 * | 1/2018 | Hansen | A61B 17/3403 |
| 2018/0078767 A1 | 3/2018 | Rapoport et al. | |
| 2018/0117309 A1 | 5/2018 | Rapoport et al. | |
| 2019/0200848 A1 * | 7/2019 | McDowall | A61B 1/00186 |

FOREIGN PATENT DOCUMENTS

| | | | | |
|---|---|---|---|---|
| WO | WO-2016126340 A2 * | 8/2016 | | A61B 5/6882 |
| WO | 2018102307 A1 | 6/2018 | | |

OTHER PUBLICATIONS

Musk, Elon, An Integrated Brain-Machine Interface Platform with Thousands of Channels, Jul. 17, 2019 bioRxiv (retrieved from the Internet http://dx.doi.org/10.1101/703801).
Hanson, Timothy et al., The "Sewing Machine" for Minimally Invasive Neural Recording, Mar. 14, 2019 bioRxiv (retrieved from the Internet http://dx.doi.org/10.1101/578542).
PCT/US2019/050858, "International Search Report and Written Opinion," dated Nov. 19, 2019, 8 pages.
PCT/US2019/050877, "International Search Report and Written Opinion," dated Dec. 5, 2019, 12 pages.
PCT/US2019/050886, "International Search Report and Written Opinion," dated Feb. 5, 2020, 15 pages.
Application No. PCT/US2019/050858, International Preliminary Report on Patentability, dated Jul. 1, 2020, 16 pages.
Application No. PCT/US2019/050877, International Preliminary Report on Patentability, dated Jul. 16, 2020, 6 pages.
PCT/US2019/050886, International Preliminary Report on Patentability, dated Mar. 25, 2021, 12 pages.

* cited by examiner

COMPUTER VISION TECHNIQUES

CROSS-REFERENCES TO RELATED APPLICATIONS

This application claims the benefit of priority of U.S. Provisional Application No. 62/731,520 titled "Computer Vision Techniques" and filed on Sep. 14, 2018, which is herein incorporated by reference in its entirety for all purposes.

STATEMENT AS TO RIGHTS TO INVENTIONS MADE UNDER FEDERALLY SPONSORED RESEARCH AND DEVELOPMENT

Not Applicable

BACKGROUND OF THE INVENTION

Surgery is a critical yet delicate activity. Accordingly, highly trained surgeons must conventionally perform surgical procedures, especially neurosurgical procedures. For example, conventional surgical techniques to implant devices into biological tissue are constrained by the necessity to properly target an insertion site for an implantable device. Improperly targeted implantable devices may cause damage to blood vessels or tissue.

Nevertheless, conventional surgical techniques are prohibitively expensive, and may limit the adoption of innovative implantable technologies, such as brain-computer interfaces. For example, human surgeons cannot reliably perform large numbers of sequential insertions of implantable electrodes into the brain.

Conventionally, robotic surgery is restricted by difficulties controlling robots in real time via standard imaging techniques, for example due to limited depth of field, glare, or reflective elements in camera images. Thus, conventional robotic surgery techniques are inferior to human surgeons in their ability to determine precise positioning of implantable devices, target tissues, and related implements such as insertion needles.

BRIEF SUMMARY OF THE INVENTION

Generally, a robotic surgery system uses fluorescence of certain elements, special lighting, and computer vision techniques to facilitate implanting a micro-manufactured biocompatible electrode device in biological tissue (e.g., neurological tissue such as the brain) using robotic assemblies. The robotic surgery system may include components to engage a tiny implantable device, identify a target implantation site in bloody or other biological tissue, and verify proper insertion. The system can attach, via robotic manipulation, the electrode to an engagement element of a miniature insertion needle. The system can illuminate metal portions of the robotic end effector with specific colors of light, such as red light, to better contrast edges and features. It can surgically implant the electrode via a robotic assembly, and based on contour images of the target tissue and a triangulated location of the electrode.

The system may irradiate a polymer portion of the electrode using a near-ultraviolet (near-UV) wavelength of light. The near-UV wavelength may be between 300 nanometers (nm) and 425 nanometers. The first light source may comprise a first light emitting diode (LED) or a first laser. The system and/or a first camera may then obtain a first image of the polymer portion with light fluoresced from the polymer portion in response to the irradiating. The system and/or a second camera may then obtain a second image of the polymer portion with the light fluoresced from the polymer portion. The system, and/or a processor using a computer vision heuristic to process the first image and the second image, may then triangulate a three-dimensional (3D) location of the electrode. The system and/or a second light source comprising a second LED or a second laser may then illuminate an insertion needle using visible light. The system and/or the first camera may then obtain a third image of the insertion needle illuminated by the visible light. Finally, the system may robotically engage the polymer portion of the electrode with the insertion needle based on the 3D location and the third image.

In some embodiments, the insertion needle comprises metal and the visible light comprises red light.

In some embodiments, the polymer portion may comprise polyimide. The near-UV wavelength of the light may be between 390 nanometers and 425 nanometers. The light fluoresced from the polymer portion may comprise green light.

In some embodiments, robotically engaging the polymer portion of the electrode may comprise robotically attaching, based on the 3D location and the third image, an engagement element of the insertion needle to a reciprocal engagement element connected with the electrode.

In some embodiments, the reciprocal engagement element may comprise a loop. Attaching the engagement element of the insertion needle to the reciprocal engagement element may further comprise threading the insertion needle through the loop.

In some embodiments, the first camera may be situated substantially perpendicular to a planar surface of a projected edge associated with the electrode. The second camera may be situated at an angle greater than 5° relative to the first camera.

In some embodiments, the second camera may be situated at an angle between 40° and 50° relative to the first camera.

In some embodiments, the system may surgically implant the electrode using the insertion needle.

In some embodiments, the system may obtain a fourth image of a target surgical tissue. The system may determine, based on the fourth image, a contour location of the target surgical tissue. Surgically implanting the electrode may further be based on the determined contour location.

In some embodiments, while surgically implanting the electrode, the system may obtain a fifth image of the electrode and the target surgical tissue. The system may verify, based on the fifth image, an implantation of the electrode.

In some embodiments, the first camera or the second camera may be integrated within a microscope.

In some embodiments, the system for robotic surgical implantation of an electrode may comprise the first light source comprising the first LED or first laser, the second light source comprising the second LED or second laser, the first camera, the second camera, and a robotic assembly. The system may further comprise the processor configured to execute computer-executable instructions that cause the processor to perform, and/or to instruct the components of the system to perform, any of the methods described above for robotic surgical implantation of an electrode.

In some embodiments, a non-transitory computer-readable medium may store computer-executable instructions that, when executed by a processor, cause the processor to perform, and/or to instruct the components of the system to perform, any of the methods described above for robotic surgical implantation of an electrode.

BRIEF DESCRIPTION OF THE DRAWINGS

The accompanying drawings, which are incorporated in and constitute a part of this specification, illustrate several embodiments and, together with the description, serve to explain the disclosed principles. In the drawings.

DETAILED DESCRIPTION OF THE INVENTION

Generally, the present disclosure is directed towards systems and methods that use computer vision techniques in association with micro-precision robotic surgery. In particular, the disclosed systems and methods may utilize specialized illumination and computer vision techniques to guide robotic assemblies in implanting tiny, bio-compatible electrode devices in biological tissue. The scale is so small that normal, white lighting does not show sharp enough edges and other features for computer vision. In some embodiments, the system can perform complex surgical tasks such as engaging and positioning an implantable device on an insertion needle, targeting and implanting the device, and/or verifying safe and proper insertion. The system can use computer vision to enhance the safe, precise, and efficient performance of any or all of these tasks.

In a non-limiting example, the disclosed system and methods may be used to implant an electrode device in neurological tissue, such as a brain. In particular, the implantable electrode device may be configured to record and/or stimulate electrical signals through regions of the brain. In further examples, the disclosed system and methods may be used to perform surgery in biological tissue including, but not limited to: the brain, muscle, liver, pancreas, spleen, kidney, bladder, intestine, heart, stomach, skin, colon, etc. Additionally, the disclosed robotic surgery systems and methods are not limited to use with humans, but can be used with any suitable multicellular organism.

In an example, a robotic surgical implantation system according to the disclosed embodiments may include an implantable device engagement sub-system, a targeting sub-system, and an insertion verification sub-system. The implantable device engagement sub-system, the targeting sub-system and the insertion verification sub-system may apply computer vision techniques to implant and verify the implantation (or insertion) of an implantable device in biological tissue (such as the brain) using robotic manipulators. In some embodiments, the implantable devices may be configured to record and/or stimulate biological tissue.

In an example automated surgical procedure, initially, the targeting sub-system of the robotic surgical implantation system may determine a target tissue site for implantation. Based on the target, the robotic surgical implantation system may position the implantable electrode device (housed in a pillbox-cartridge assembly) and a needle in the surgical field. As disclosed herein below, the device engagement sub-system may use computer vision and robotic engagement to engage the needle with the implantable device. The robotic surgical implantation system may then implant the device and needle into the target biological tissue. The insertion verification sub-system may then verify implantation of the device into the target tissue, as disclosed herein.

Figure 1A:
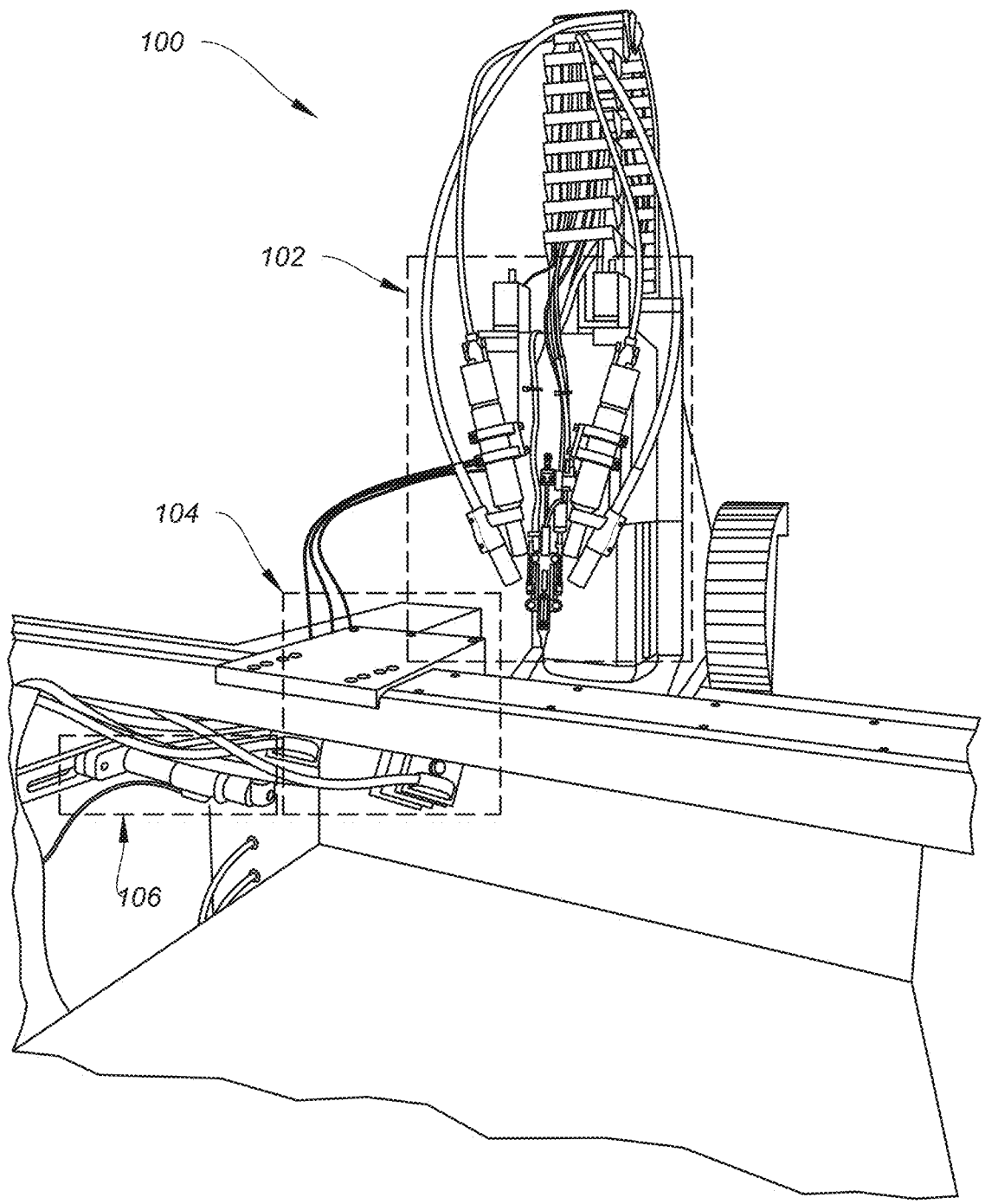
FIG. 1A illustrates an example system for robotic surgical implantation of an electrode, according to an embodiment.
Figure 1B:
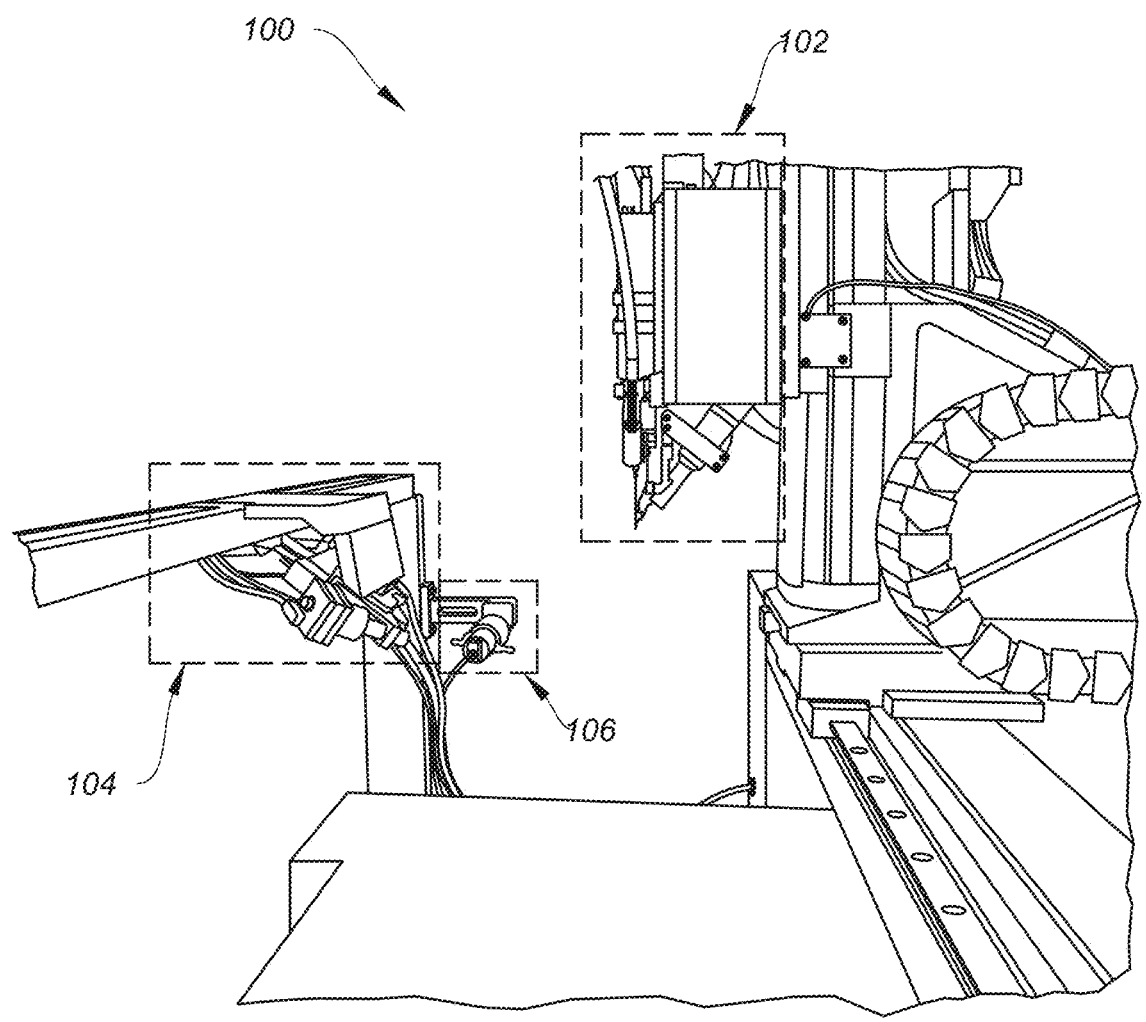
FIG. 1B illustrates a side view of the system in FIG. 1A.

FIG. 1A illustrates an example system 100 for robotic surgical implantation of an electrode device, according to an embodiment. FIG. 1B illustrates a side view of example system 100 for robotic surgical implantation of an electrode, according to an embodiment. In some embodiments, the entire system 100 may be associated with a robot, for example a single robot may be integrated together with all the components of system 100. In some embodiments, some sub-systems of system 100 may be combined, for example a single robot may include an inserter head 102 that can also perform the functions of device engagement sub-system 104, and is not limited by the present disclosure.

In this example, system 100 includes an inserter head 102 and device engagement sub-system 104. Device engagement sub-system 104 can engage electrodes for implantation, and inserter head 102 can perform targeting and/or insertion verification functions while implanting the electrodes in neurological tissue, as described herein below. Inserter head 102 may also be referred to as a targeting and/or insertion verification sub-system, and device engagement sub-system 104 may also be referred to as an electrode stage. In some embodiments, the functions of inserter head 102 and device engagement sub-system 104 can instead be performed by a single apparatus. For example, in some embodiments, the functions of device engagement sub-system 104 may be performed by components of inserter head 102. System 100 may further include ultrasonic cleaner 106.

System 100 and/or sub-system 104 can contain light sources configured to illuminate the electrode device and system 100 and/or sub-system 102 can contain light sources configured to illuminate the surgical field. The light sources illuminating the electrode device or an insertion needle can produce light of wavelengths selected based on a material associated with the electrode device or needle, while the light sources illuminating the surgical field can produce light of wavelengths chosen for imaging the target tissue. In particular, system 100 may contain multiple independent light modules, each capable of independently illuminating with 405 nm, 525 nm and 650 nm or white light. For example, if the implantable electrode device contains a bio-compatible substrate made from polyimide, the wavelength of the light from the light source may be between 390 nm and 425 nm (e.g., 405 nm or 395 nm). In an embodiment, the light sources may include a laser and/or a light emitting diode (LED). In an embodiment, the implantable electrode device can contain a bio-compatible substrate made from polyimide, polyamide, and/or another aromatic rigid chain polymer material, fluorescent material, or other material, and is not limited by the present disclosure.

System 100 can contain cameras configured to obtain images, such as digital photos, of the electrode device and an insertion needle, and cameras configured to obtain images of the target neurological tissue, e.g. a brain cortex. In another example, the images can include images of any subject relevant to robotic surgical implantation. In a typical embodiment, the cameras can include two cameras arranged at a relative angle (e.g., a relative angle substantially equal to 450, or some other angle). In various embodiments, system 100 can contain additional cameras, or other sensors, such as video cameras, microphones, chemical sensors, temperature sensors, time sensors, and force or pressure sensors, and is not limited by the present disclosure.

The light sources may include one or more light sources that can be cycled or strobed between illuminated and extinguished states, and/or among different wavelengths of light, so that the cameras can image different perspectives or aspects of the surgical field. In an embodiment, the cameras can be cooled in order to increase their sensitivity, such as to faint fluorescent light. In one embodiment, one or more of the cameras may be integrated into a microscope.

System 100 can include a processing unit, such as computing system 1008 in the example of FIG. 10 below or computing system 1500 in the example of FIG. 15A below, configured to execute a computer vision heuristic to process the images obtained by the cameras. The computing system may be communicatively coupled to a plurality of cameras configured to image one or more portions of the surgical field and/or the electrode device and needle. In particular, the computing system can apply computer vision techniques to images from the cameras in order to determine the location and/or orientation of the electrode device. In an embodiment, the computing system can determine locations and/or orientations of an insertion needle and a target tissue for implantation. For example, the computing system can determine a contour of the target surgical tissue, based on images from the cameras. In various embodiments, a processing unit can include one or more processors, one or more processing cores, one or more computing systems such as computing system 1500 in the example of FIG. 15A below, one or more GPUs, or combinations thereof, and is not limited by the present disclosure.

System 100 can contain one or more robotic assemblies, such as a robotic assembly configured to implant the electrode device surgically into target biological tissue. The robotic assemblies may be guided by a processing unit, such as computing system 1500 in the example of FIG. 15A below, based on the triangulated locations of the electrode device, an insertion needle, and/or a target tissue, determined by the computing system. In an embodiment, system 100 can further contain an additional robotic assembly configured to attach an engagement element of the insertion needle to a reciprocal engagement element on the electrode device. In an embodiment, when surgically implanting the electrode device, the robotic assemblies can surgically implant the insertion needle attached to the electrode device. The robotic assemblies can further be guided based on images from the cameras. In an embodiment, system 100 can contain other actuators, such as sonic, ultrasonic, or pressure actuators, or can guide other implements such as a scalpel, and is not limited by the present disclosure.

In some embodiments, system 100 can include additional cameras, and is not limited by the present disclosure. For example, system 100 can use a separate camera system, located on a head of a robotic assembly, for mapping the target tissue site. In some embodiments, this robotic assembly may also be configured to carry an insertion needle. The separate camera system can be movably situated on one or more axes. In an embodiment, the system drives this robotic assembly down an axis, such that a focus of the camera system is below the target tissue site of interest, such as brain tissue. The robotic assembly can move upward along the axis, and/or scan the camera system upwards, in order to image the target tissue.

In a typical embodiment of the present disclosure, robotic surgery system 100 may implant implantable devices including electrodes with improved depth penetration that are able to penetrate below the surface of biological tissue (e.g., cortex). Example electrodes may include those discussed in a U.S. patent application titled "Electrode Design and Fabrication," filed concurrently herewith, and hereby incorporated by reference. The disclosed robotic system may implant implantable devices that are arranged in a pillbox, a cartridge, and/or a pillbox-cartridge assembly such as those discussed in a U.S. patent application titled "Device Implantation Using a Cartridge," filed concurrently herewith, and hereby incorporated by reference. Additionally, the disclosed robotic system may control the operation of a needle.

I. Targeting Components

Figure 2:
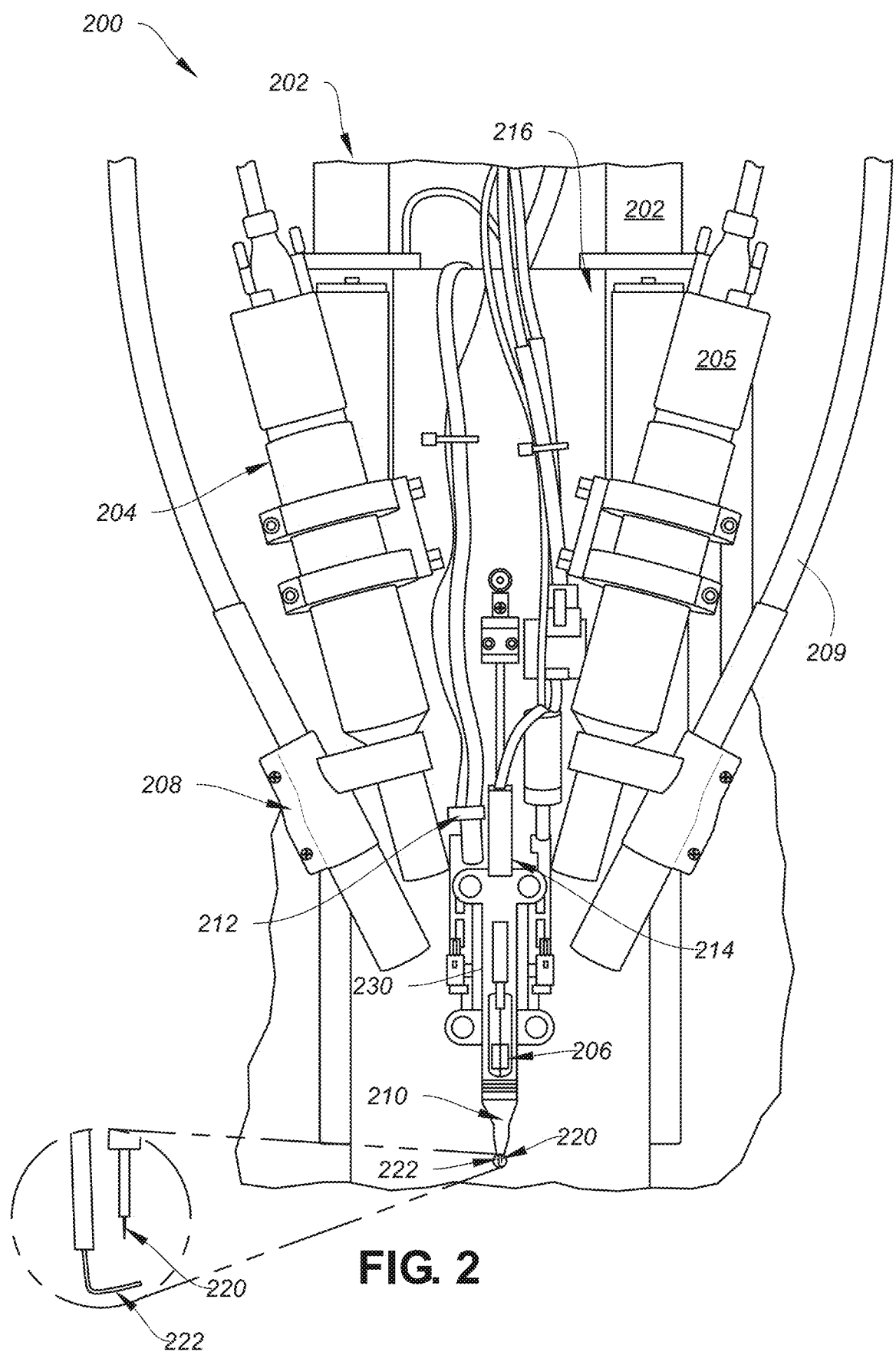
FIG. 2 illustrates an example system for targeting of tissue for robotic surgical implantation of an electrode, according to an embodiment.

FIG. 2 illustrates an example system 200 for targeting of tissue for robotic surgical implantation of an electrode, according to an embodiment. As described above, the targeting sub-system can determine a target tissue site for implantation, position the implantable electrode and needle in the surgical field, and implant the device and needle into the target biological tissue. In this example, the targeting components may include light sources 208 and 209, one or more cameras, such as cameras 204 and 205, and a processing unit such as a computing system that is configured to select regions of biological tissue at which one or more implantable electrode devices may be inserted.

In some embodiments, light sources 208 and 209 and cameras 204 and 205 are coupled to the computing system. In some embodiments, the computing system may be a microprocessor controller 216. In other embodiments, the computing system may be computing system 1008 in the example of FIG. 10, or computing system 1500 in the example of FIG. 15A, below, or may communicate with these systems. The computing system may include computer software that provides a user interface configured to display the images obtained by cameras 204 and 205. In some embodiments, the cameras may be integrated into a microscope. Cameras 204 and 205 may be configured to image the surface of the biological tissue in the surgical field. Cameras 204 and 205 may also include one or more polarization filters that can be applied to the obtained image. Such polarization filters can reduce glare and the effect of reflected light in the observed image. In this example, the targeting sub-system 200 also includes insertion camera stack 206 behind a mounting plate. In an embodiment, targeting sub-system 200 can also include a camera with a wide-angle view of the surgical field.

In some embodiment, camera 204 and/or camera 205 can be cooled in order to increase their optical and/or imaging sensitivity. In an embodiment, cameras 204 and/or 205 can be sensitive enough to generate a detailed three-dimensional map of a plurality of electrodes implanted in the target tissue site. Cameras 204 and/or 205 can be cooled and/or maintained at low temperatures by refrigeration systems, cooling fluids such as liquid Nitrogen and/or Hydrogen, or any other cooling methods, not limited by the present disclosure.

In this example, light sources 208 and 209 are located near cameras 204 and 205, respectively. This proximity may provide technical advantages because it requires less energy to illuminate the target brightly, and produces fewer shadows. In some embodiments, the light sources may instead be spread about the apparatus, and are not limited by the present disclosure. Cameras 204 and 205 can be independently controlled, panned, oriented, and/or focused by targeting camera actuators 202.

In some embodiments, the light sources may be configured to apply light in a way that can differentiate biological tissue and features such as blood vessels. In particular, the targeting components may image blood vessels, so that the robotic surgery system can avoid damaging the blood vessels during the surgical implantation procedure. For example, in one embodiment, light sources 208 and 209 may be configured to light the surgical field with amber light having a wavelength of approximately 590 nanometers. The amber light may be absorbed by hemoglobin such that the image obtained by the cameras can be used to differentiate between biological tissue and blood vessels. In another example, light sources 208 and 209 can use green light having a wavelength of approximately 525 nanometers, in order to provide sufficient contrast for viewing blood vessels. In a third example, light source 208 can use light that will be absorbed by material in the electrodes, such as polyimide, causing the material to fluoresce. In various embodiments, the electrodes can contain fluorescent aromatic rigid chain polymers such as polyimide, or can contain polyimide, and/or other fluorescent materials or fluorescent molecules, and are not limited by the present disclosure. In an embodiment, the fluoresced light may be of longer wavelength than the absorbed light. Cameras 204 and 205 can capture light fluoresced by the material in order to generate a three-dimensional map of a plurality of electrodes implanted in biological tissue 208, such as a brain.

The inserter head of the targeting sub-system 200 can include an imaging stack, such as cameras 204, 205, and insertion camera stack 206, used for guiding the needle into the thread loop, insertion targeting, live insertion viewing, and insertion verification. In addition, the inserter head can contain a number of independent light modules (e.g., six or any other number of light modules), such as light sources 208 and 209, each capable of independently illuminating with 405 nm, 525 nm and 650 nm or white light. Stereoscopic cameras, software based monocular extended depth of field calculations, and illumination with 525 nm light allow for precise estimation of the location of the cortical surface. In some embodiments, the device engagement function, as described below, may be performed by the inserter head 200, using the 405 nm light.

The image obtained by camera 204 may be transmitted to the computing system. In an embodiment, the computing system can apply a filter, such as a spatial band pass filter, to identify blood vessels based on their length scale. In some embodiments, the computing system may process the obtained images such that biological structures and tissue are distinguishable within the image, or can determine a contour or surface map of biological tissue 208, such as the exterior contours of a brain, or a particular target site within biological tissue 208. In an embodiment, the computing system can form a composite image (e.g., a stereo composite image) based on target tissue images from multiple cameras (e.g., a left and a right camera), thereby providing Extended Depth of Field (EDF) information.

Using the user interface on the computing system, a user may select target locations for implantation of one or more implantable electrode devices. In some embodiments, the computer software may automatically propose one or more target locations for implantation. The user interface may be configured such that the user of the computing system may provide approval of the automatically generated proposed target locations. Such automatically generated proposed target locations can be based on the obtained image, e.g., by applying computer vision, artificial intelligence, or machine learning heuristics to the image. The computing system may propose target locations that avoid vasculature, are geometrically advantageous for recording and/or stimulating sites of interest, and/or are a minimal distance apart. In some embodiments, the computing system can apply such heuristics to determine and/or select a target site automatically, and does not require input from a user. In some embodiments, the computing system can further position a robot assembly, instruct camera 204 to scan the surgical field, and locate a target tissue such as a brain in a composite image.

The inserter head of the targeting sub-system 200 can also hold a needle pincher cartridge (NPC) 210, as described further in the example of FIG. 7 below, a pincher actuator 212, and a needle actuator 214 with inline force sensor. The NPC may include a needle 220 and needle pincher 222.

II. Implantable Device Engagement Components

Figure 3:
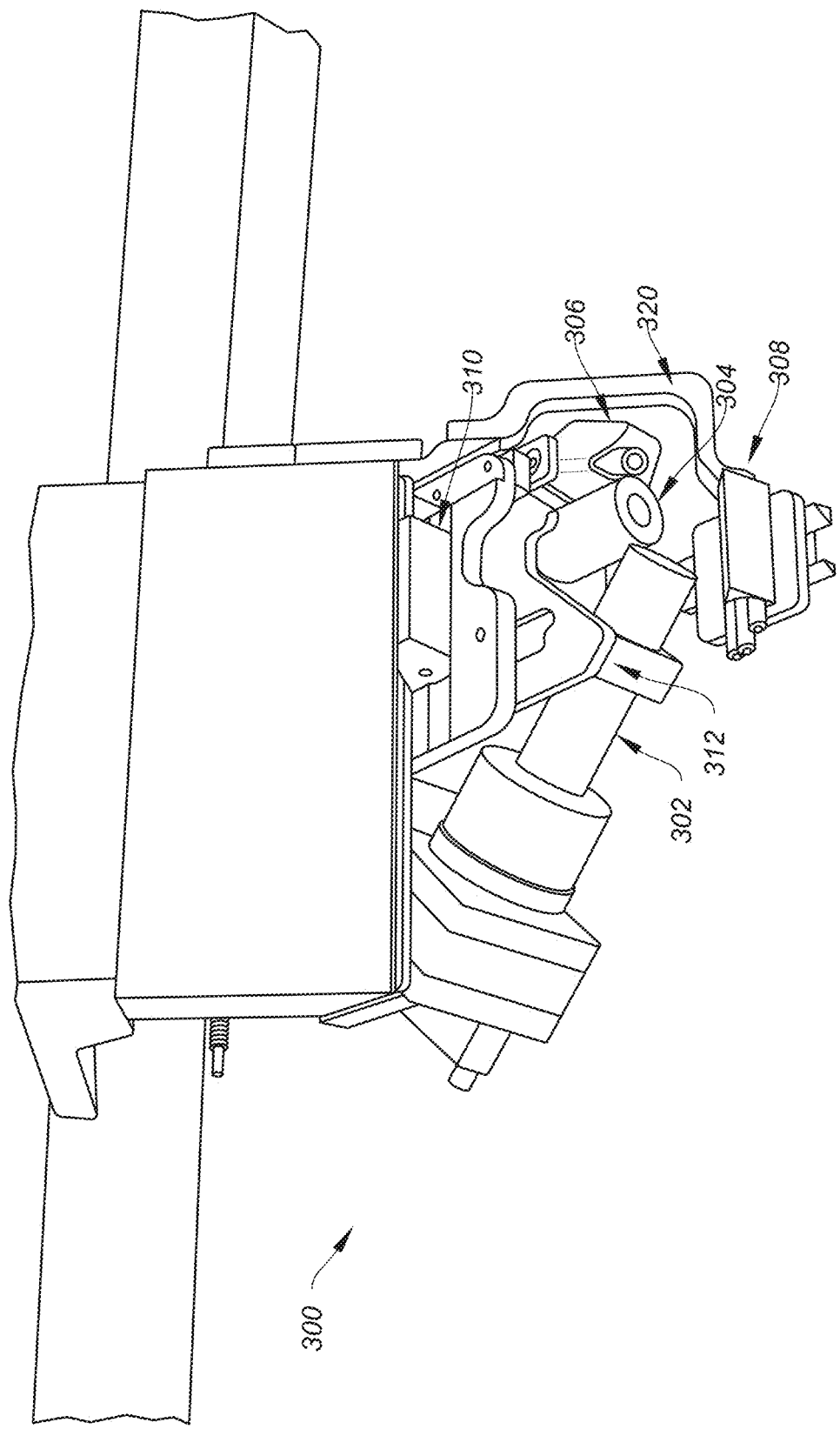
FIG. 3 illustrates an example system for visualization and robotic engagement of an electrode, according to an embodiment.

FIG. 3 illustrates an example system 300 for visualization and robotic engagement of an electrode, according to an embodiment. In the example of FIG. 3, device engagement sub-system 300 is shown as a separate system. However, note that in some embodiments, the functions of the inserter head and the device engagement sub-system 300 can instead be performed by a single apparatus. For example, in some embodiments, the functions described here as performed by device engagement sub-system 300 may instead be performed by components of the inserter head, or of a single integrated robotic surgery and computer vision system. Alternatively, the components described here as part of device engagement sub-system 300 may be integrated into the inserter head or a single system.

In this example, the device engagement components include cameras 302 and 304 configured to obtain images that are used to observe and guide robotic assemblies (e.g., robotic manipulators, etc.), to detachably couple an engagement element of an implantable electrode device with a reciprocal engagement element of an insertion needle. In some embodiment, the robotic assemblies used to engage the electrode with the needle may be part of the inserter head, such as inserter head 200 in the example of FIG. 2, but may be controlled by the system based on images obtained by cameras 302 and 304 of the device engagement sub-system 300. In another embodiment, the cameras used to guide device engagement may instead be situated on the inserter head, or alternatively, both the device engagement sub-system 300 and the inserter head may be integrated into a single robotic surgery system.

The insertion needle may be configured to engage with the implantable electrode device, for example, the needle may be threaded through a polyimide loop on the electrode. In an embodiment, the loop may measure approximately (16×50) µm². Alternatively, in various embodiments, the respective engagement elements may include a hook, a cup, a protrusion, an extended arm, a "v," etc. The implantable device engagement components may also include one or more light sources, such as light source 306, configured to light the surgical field, and to illuminate or irradiate the electrode device and insertion needle while they are imaged by cameras 302 and 304.

As illustrated in FIG. 3, a plurality of implantable electrode devices may be arranged in a cartridge-pillbox assembly 308, and engagement features for the electrodes may be arranged on the cartridge portion. The positions of the cartridge-pillbox assembly 308 and the insertion needle may be controlled by one or more of the robotic assemblies. In various embodiments, the robotic assemblies can include robotic arms, robotic manipulators, or any other robotic apparatus, and are not limited by the present disclosure.

During robotic engagement, the robotic assemblies can be guided by a processing unit or computing system, which can process the images using computer vision techniques. The robotic assemblies may be communicatively coupled to the processing unit, such as computing system 1008 in the example of FIG. 10 below, or computing system 1500 in the example of FIG. 15A below. The computing system may be configured to receive information from the robotic assemblies regarding their positions, orientations, etc. The computing system may also be communicatively coupled to a plurality of cameras, such as cameras 302 and 304, configured to image the implantable devices on the cartridge and/or the needle. The computing system may also be configured to transmit signals to the robotic assemblies to control their position. In various embodiments, these instructions can include low-level instructions to undertake specific motions or high-level instructions that can be interpreted by the robotic assemblies.

In a typical embodiment, the engagement features (e.g., loops) of a plurality of implantable electrode devices are held stationary on the cartridge. The system can use computer vision techniques to drive the needle into alignment with the engagement features based on the images of the needle and engagement features taken by cameras 302 and 304. Once the needle is inserted into the loop, a needle pincher, such as needle pincher 702 in the example of FIG. 7 below, can extend from a needle pincher cartridge (NPC) and rotate toward the needle. The NPC is the portion of the inserter head 200 that makes direct contact with the target tissue. The pincher can rotate to pinch the neck of the electrode loop against a cannula tip of the needle as the NPC peels the electrode's thread off of a parylene backing, and drives the thread to the insertion site on the target tissue. The robotic assembly can then drive the NPC to the target tissue, where the needle extends through the cannula and enters the tissue. The electrode and loop can then remain in the tissue, as the needle retracts for reuse. In an embodiment, the NPC is a consumable that can be replaced during surgery in under a minute.

In some embodiments, light source 306 may be configured to apply a light that enhances the imaging of the engagement features. For example, light source 306 can produce light of wavelengths selected based on a material associated with the implantable electrode device or materials included in the engagement features. For example, near-ultraviolet (near-UV) light may be absorbed by polyimide used in manufacturing the engagement feature. In particular, irradiation by these wavelengths can excite fluorescence from the polyimide, thereby enabling cameras 302 and 304 to resolve the edges of the polyimide much more sharply. In various examples, the near-UV light may have a wavelength between 300 nm and 425 nm, or between 390 nm and 425 nm, such as approximately 405 nm. In another example, some other wavelength may be used, such as 395 nm, or the system may use a combination of wavelengths or may cycle among different types of light, such as between near-UV light and monochromatic visible light. The near-UV illumination allows the optical stack and computer vision to reliably localize the thread loop and execute sub-micron visual servoing to thread or guide the needle through it. In an embodiment, this servoing can be illuminated by 650 nm light.

Alternatively, the light source 306 may apply visible light, such as red light, which is particularly useful for imaging the insertion needle, or white light. Using red light can provide a technical advantage by reflecting more strongly and clearly from metal that comprises the needle, and may enable the cameras 302 and 304 to resolve the needle tip clearly. In various embodiments, multiple light sources may be used to apply different types of light, or the light source may cycle among the different types of light.

Light source 306 may a laser and/or a light emitting diode (LED). In this example, light source 306 is a light pipe. In other examples, the light source 306 may include independent light modules.

In some embodiments, cameras 302 and 304 can be configured at an angle to each other (e.g., this angle can be approximately 45°, or any other angle, and is not limited by the present disclosure). In an embodiment, a first front view camera, such as camera 304, may be configured to image the engagement features of the plurality of implantable devices arranged on a cartridge in a front view. A second side view camera, such as camera 302, may be configured to image the engagement features of the plurality of implantable devices arranged on the cartridge in a side view. By combining these multiple views using computer vision techniques, the system can triangulate a three-dimensional (3D) location of the electrode device, insertion needle, and/or any other object. In some embodiments, cameras 302 and 304 may be configured to move in relation to the surgical field, and more particularly, the pillbox-cartridge assembly. In particular, the cameras can be panned and focused via pan actuation assembly 310 and focus actuation assembly 312, respectively.

In some embodiments, a different number or configuration of cameras may be used. For example, the cameras focused on the electrode threads can be located directly on the inserter head of the targeting sub-system 200 of the example of FIG. 2, rather than on a separate device engagement sub-system assembly 300. Alternatively, in an embodiment, the cameras used to guide device engagement may instead be situated on the inserter head, or both the device engagement sub-system 300 and the inserter head may be integrated into a single robotic surgery system.

In an embodiment, the cameras can be on independent motion axes and/or in different angular configurations, and are not limited by the present disclosure. In an embodiment, one or more of the cameras may be integrated into a microscope.

In an embodiment, the one or more light sources, such as light source 306, may be cycled between illuminated and extinguished states, and/or cycled among different wavelengths of light. For example, one or more light sources can be cycled or strobed between light to be absorbed by a material in the electrode device (e.g., near-UV light with approximately 395 nm or 405 nm wavelength) and light used to illuminate the insertion needle (e.g., red light). Thus, the different lights can be used to image different objects. In an example, two separate light sources (e.g., any combination of lasers and/or LEDs) can produce light to be absorbed by the electrode device and light to illuminate the insertion needle, respectively. These two light sources can be strobed on and off with alternating timing, such that only one light source is illuminated at any given time. In an embodiment, such cycling or strobing provides opportunities for separate cameras, such as camera 302 and camera 304, to image different perspectives and/or different aspects of the surgical field, electrode device, and insertion needle. For example, cameras 302 and 304 can be configured at a relative angle (e.g., approximately 45°, or some other angle), and can image the electrode device and insertion needle under different strobed lights. In an embodiment, the cycling or strobing can be rapid.

In this example, light source 306 is located near cameras 302 and 304. This proximity may provide technical advantages because it requires less energy to illuminate the target brightly, and produces fewer shadows. In some embodiments, the light sources may instead be spread about the apparatus, and are not limited by the present disclosure.

In an embodiment, camera 302 and/or camera 304 can be cooled in order to increase their optical and/or imaging sensitivity. For example, one of the cameras may be cooled in order to increase its sensitivity to relatively faint fluorescence from the electrode device, such as from polyimide contained in the electrode device. In an embodiment, cameras 302 and/or 304 can be sensitive enough to image the microscopic electrode engagement features and the insertion needle. Cameras 302 and/or 304 can be cooled and/or maintained at low temperatures by refrigeration systems, cooling fluids such as liquid Nitrogen and/or Hydrogen, or any other cooling methods, not limited by the present disclosure.

Figure 4:
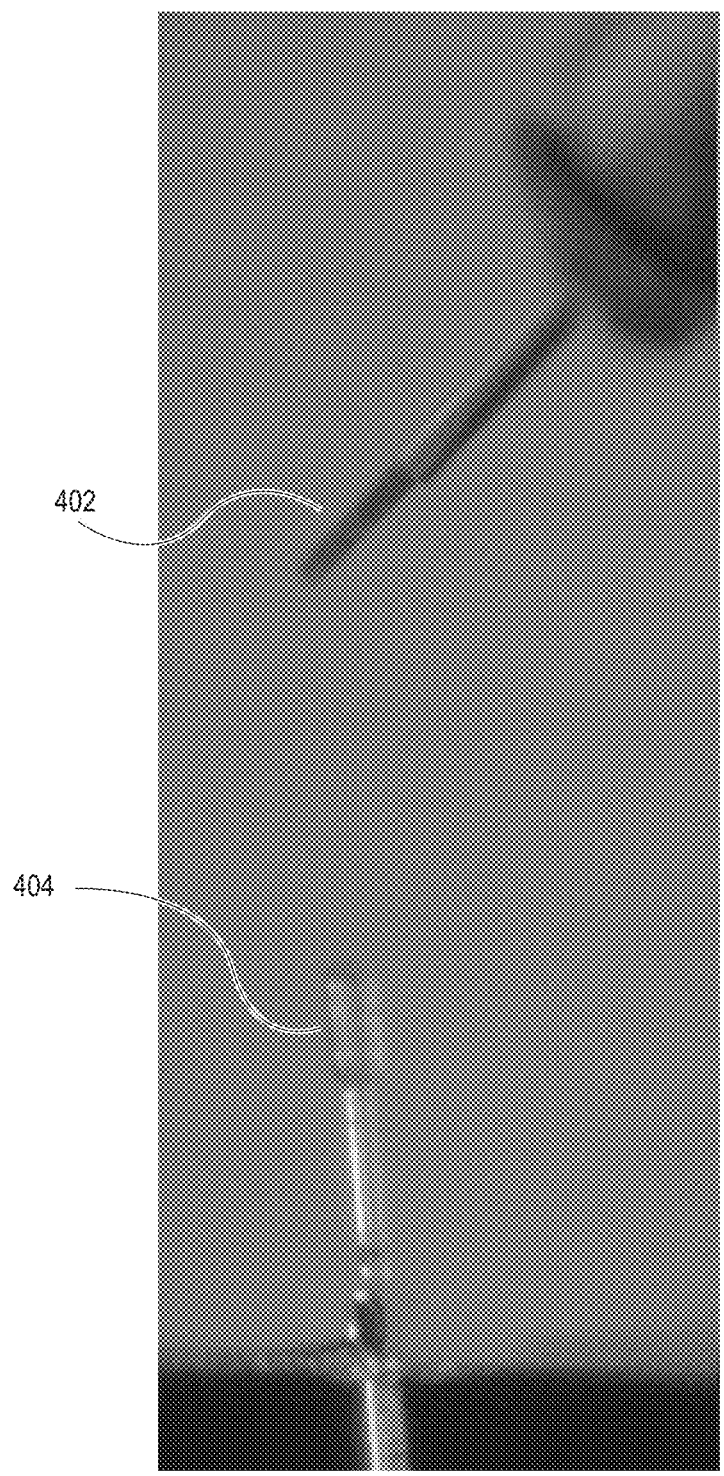
FIG. 4 illustrates an example image of a needle and an engagement component illuminated by white light, according to an embodiment.

FIG. 4 illustrates an example image of a needle 402 and an engagement component 404 illuminated by white light, according to an embodiment. In this example, the image has been taken by cameras in the device engagement system, such as cameras 302 and 304 in the example of FIG. 3, and under illumination with white light. As can be seen, the needle 402 and engagement component 404 appear blurry in this image, and it may be difficult for the system to discern the loop of engagement component 404. Likewise, needle 402 appears dimly lit. In an example, the computer vision techniques and implantable device engagement sub-system may not be able to determine the positions and orientations of needle 402 and engagement component 404 reliably enough to engage them. In particular, it may be important to avoid erroneous detections of the needle 402 and engagement component 404, such as false positive or negative detections, etc. Accordingly, in some embodiments, the system may use a monochromatic light source and/or another special light source, such as a source of near-UV radiation, in order to image the needle 402 and engagement component 404.

Figure 5:
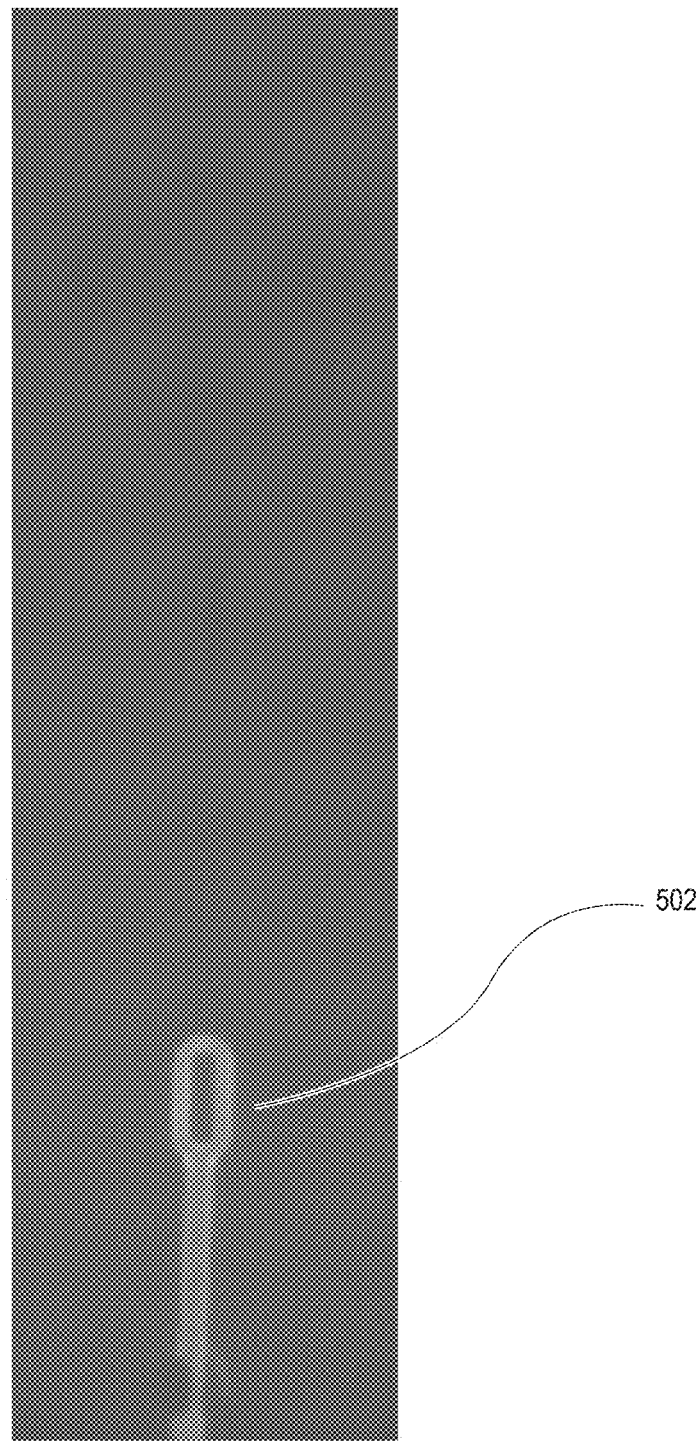
FIG. 5 illustrates an example image of an engagement component fluorescing in response to irradiation, according to an embodiment.

FIG. 5 illustrates an example image of an engagement component 502 fluorescing in response to irradiation, according to an embodiment. In this example, the engagement component 502 fluoresces green light in response to irradiation with near-UV wavelengths, such as 405 nm. The image has been taken by cameras in the device engagement system, such as cameras 302 and 304 in the example of FIG. 3, based on the green light fluoresced by engagement component 502. As can be seen, the engagement component 502 appears sharper than in the example of FIG. 4, which may thereby allow the system to locate it more accurately.

In some embodiments, the system may use black and white images for computer vision. Alternatively, the system may use color data for the computer vision. By using color images, the system may be able to make use of additional information compared with a black and white image. In this example, because the polyimide loop fluoresces green light, the color data of the image may help the system to identify the device engagement component 502, and/or to distinguish device engagement component 502 from other objects in the image.

Figure 6:
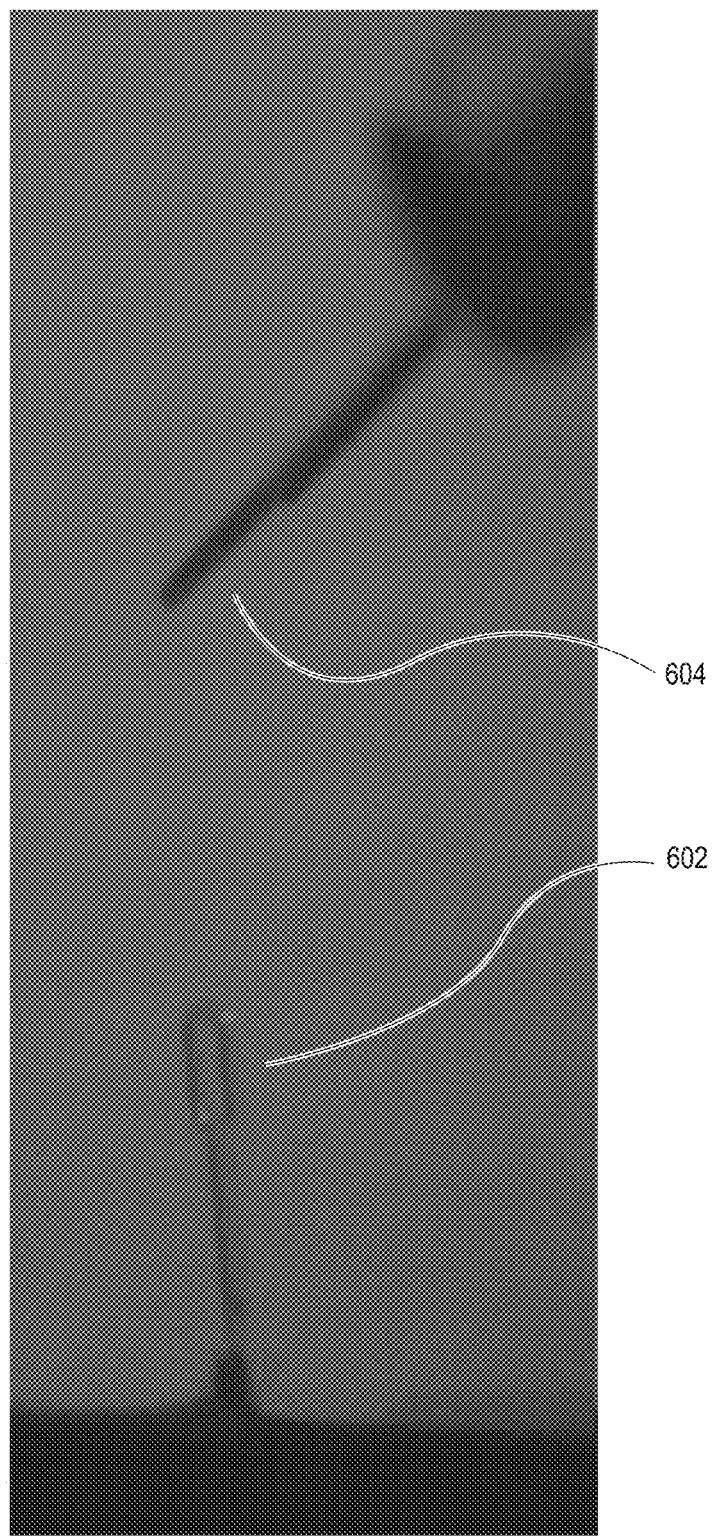
FIG. 6 illustrates an example image of a needle and an engagement component taken using red light, according to an embodiment.

FIG. 6 illustrates an example image of a needle 602 and an engagement component 604 taken using red light, according to an embodiment. In this example, the image has been taken by cameras in the device engagement system, such as cameras 302 and 304 in the example of FIG. 3, using the red light. In some cases, the image may also be taken using a red background.

Using red light can provide a technical advantage by reflecting more strongly and clearly from metal that comprises needle 602. As can be seen, the needle 602 appears sharper than in the example of FIG. 4, which may thereby allow the system to locate it more accurately. In particular, using red light together with a red backing may enable the cameras to resolve images with very defined edges of the needle tip. Accordingly, in some embodiments, the system uses red light in order to detect the position and/or orientation of the tip of needle 602. Using red light may help avoid erroneous detections, false positive or negative detections, etc.

In some embodiments, the system may use black and white images for computer vision. Alternatively, the system may make use of color data for the computer vision.

III. Electrode Implantation

The system can use a robotic insertion approach for inserting flexible probes, allowing rapid and reliable insertion of large numbers of polymer probes targeted to avoid vasculature and record from dispersed brain regions. The robot's insertion head may be mounted on a travel stage. For example, a 10 μm globally accurate, 400 mm×400 mm×150 mm travel three axis stage may be used. In various embodiments, the insertion head may be mounted on another travel stage, and is not limited by the present disclosure. The insertion head may hold a small, quick-swappable needle-pincher assembly, as described herein below.

Figure 7:
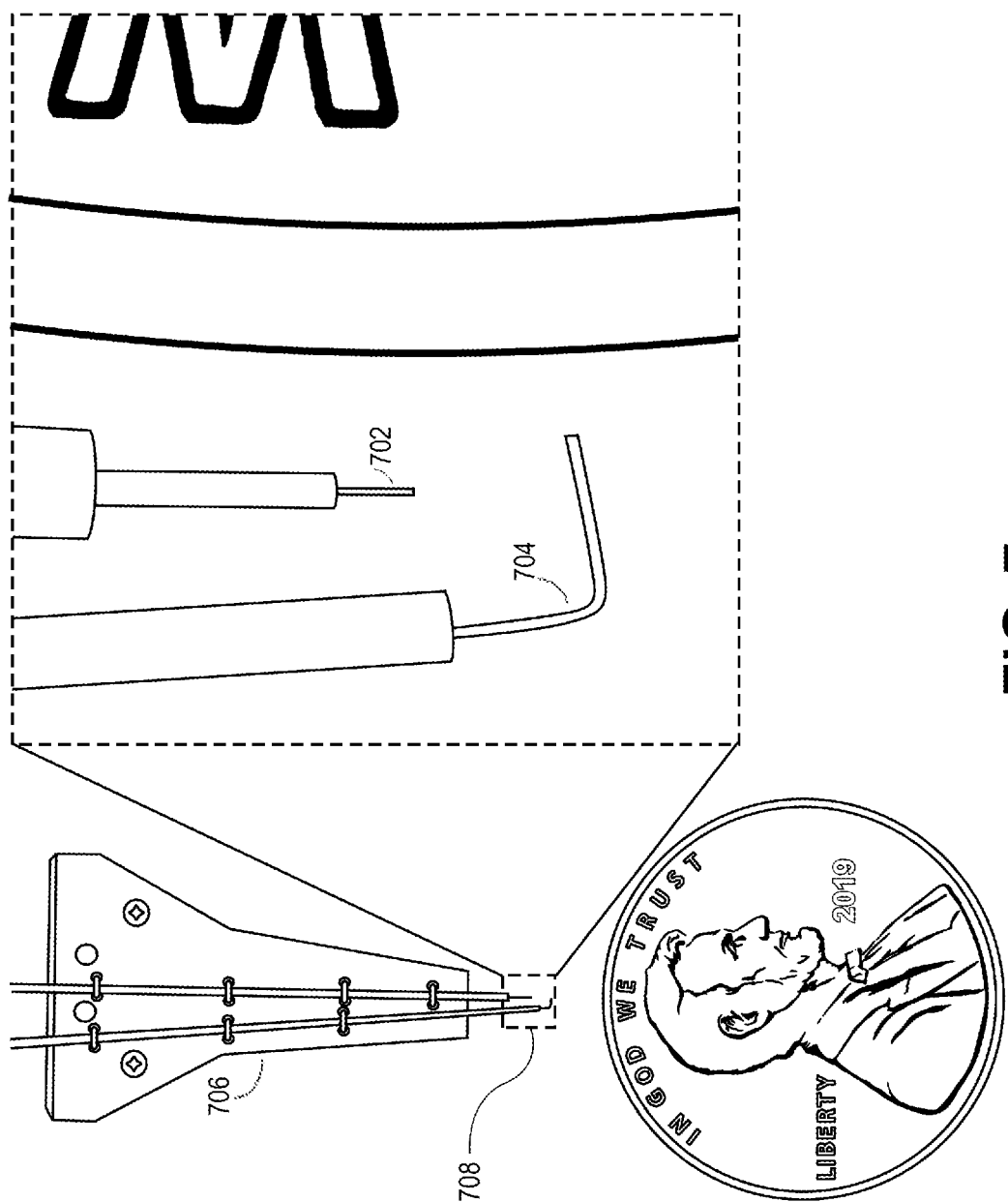
FIG. 7 illustrates an insertion needle and pincher on a needle pincher cartridge, according to an embodiment.

FIG. 7 illustrates an insertion needle 702 and pincher 704 on a needle pincher cartridge (NPC) 706, according to an embodiment. The NPC 706 is the portion of the inserter head 200 that makes direct contact with the target tissue. In an embodiment, the NPC 706 is a consumable that can be replaced mid-surgery in under a minute. The needle 702 can be milled from 40 μm diameter tungsten-rhenium wire-stock electrochemically etched to 24 m diameter along the inserted length. The tip of the insertion needle 702 is designed to engage with a reciprocal engagement component of an electrode for transporting and inserting individual threads, such as by hooking onto the insertion loop in the example of FIG. 5. The tip of needle 702 is further designed to penetrate the meninges and brain tissue. The insertion needle can be driven by a linear motor allowing variable insertion speeds and rapid retraction acceleration (up to 30,000 mm/s$^2$) to encourage separation of the probe from the needle. The pincher may be a 50 μm tungsten wire bent at the tip and driven both axially and rotationally. It serves as support for probes during transport and as a guide to ensure that threads are inserted along the needle path.

During engagement and insertion, the pincher can rotate to pinch the neck of the electrode loop against a cannula tip of the needle as the NPC peels the electrode's thread off of a parylene backing, and drives the thread to the insertion site on the target tissue. The robotic assembly can drive the NPC to the target tissue, where the needle extends through the cannula and enters the tissue. The electrode and loop can then remain in the tissue, as the needle retracts for reuse.

Figure 8:
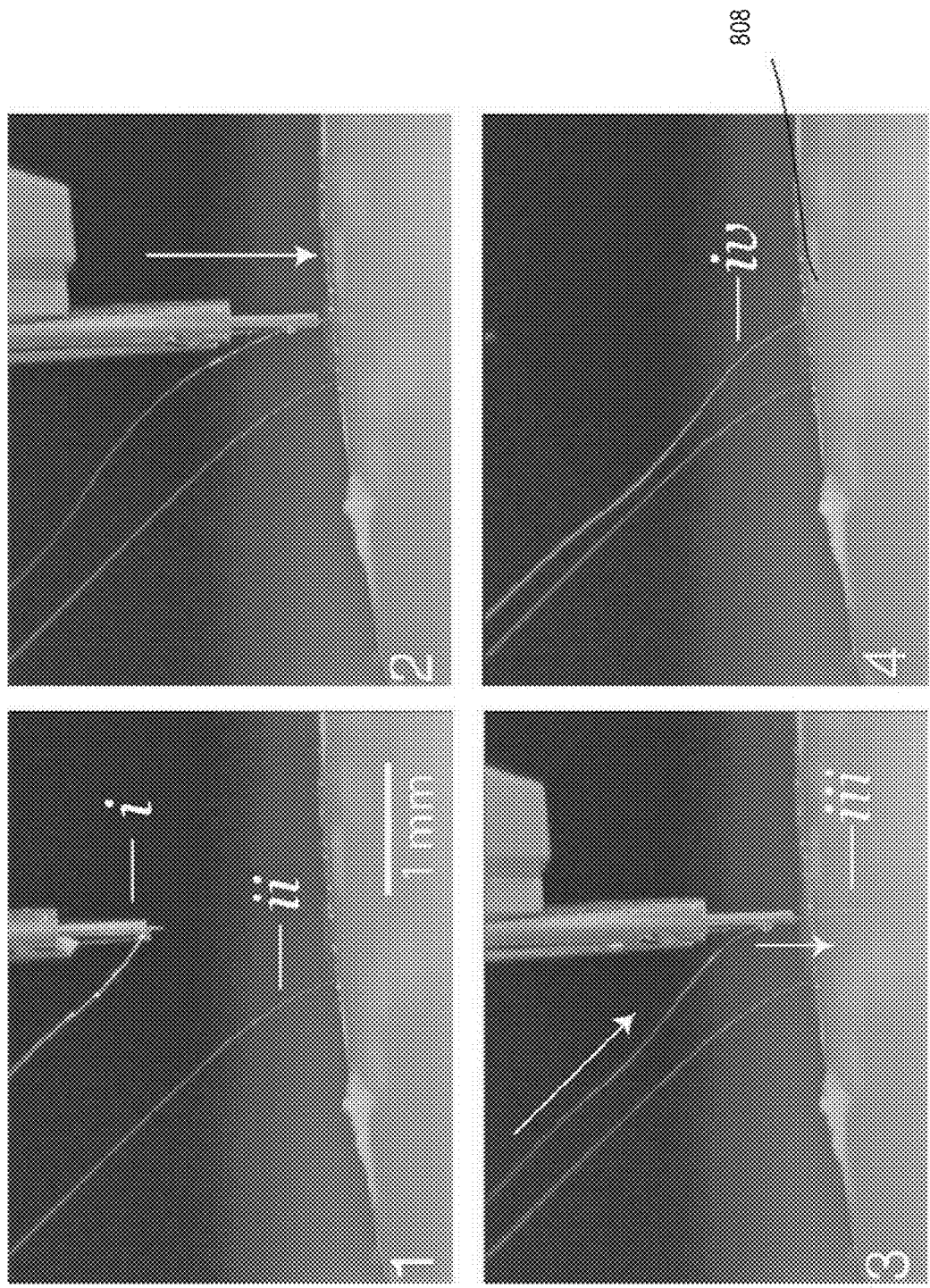
FIG. 8 illustrates implantation of electrodes in a target tissue proxy substance, according to an embodiment.

FIG. 8 illustrates implantation of electrodes in a target tissue proxy substance 808, according to an embodiment. In particular, FIG. 8 shows a sequence of steps of the insertion process into an agarose brain tissue proxy. In this example, the needle first inserts a first thread, which can hold a plurality of electrodes (e.g., 32 electrodes), and then inserts a second thread, holding a second plurality of electrodes.

The inserter head holds an imaging stack, such as cameras 204, 205, and 206 in the example of FIG. 2, used for guiding the needle into the thread loop, insertion targeting, live insertion viewing, and insertion verification. In addition, the inserter head contains light modules, such as light sources 208 in the example of FIG. 2, each capable of independently illuminating with 405 nm, 525 nm and 650 nm or white light. As described in the examples of FIGS. 3 and 5 above, the 405 nm illumination excites fluorescence from polyimide and allows the optical stack and computer vision to reliably localize the (16×50) μm$^2$ thread loop and execute sub-micron visual servoing to guide, illuminated by 650 nm the needle through it. Stereoscopic cameras, computer vision methods such as monocular extended depth of field calculations, and illumination with 525 nm light can allow for precise estimation of the location of the cortical surface.

The robot registers insertion sites to a common coordinate frame with landmarks on the skull, which, when combined with depth tracking, enables precise targeting of anatomically defined brain structures. Integrated custom computer instructions may allow pre-selection of all insertion sites, enabling planning of insertion paths optimized to minimize tangling and strain on the threads. The planning feature highlights the ability to avoid vasculature during insertions, one of the key advantages of inserting electrodes individually. This may provide a technical advantage, in order to avoid damage to the blood-brain barrier and thereby reduce inflammatory response. In an embodiment, the robot can feature an auto-insertion mode, which can insert up to 6 threads (192 electrodes) per minute. While the entire insertion procedure can be automated, a surgeon can retain control, and can make manual micro-adjustments to the thread position before each insertion into the target tissue, such as a cortex. The neurosurgical robot is compatible with sterile shrouding, and has features to facilitate successful and rapid insertions such as automatic sterile ultrasonic cleaning of the needle.

Figure 9:
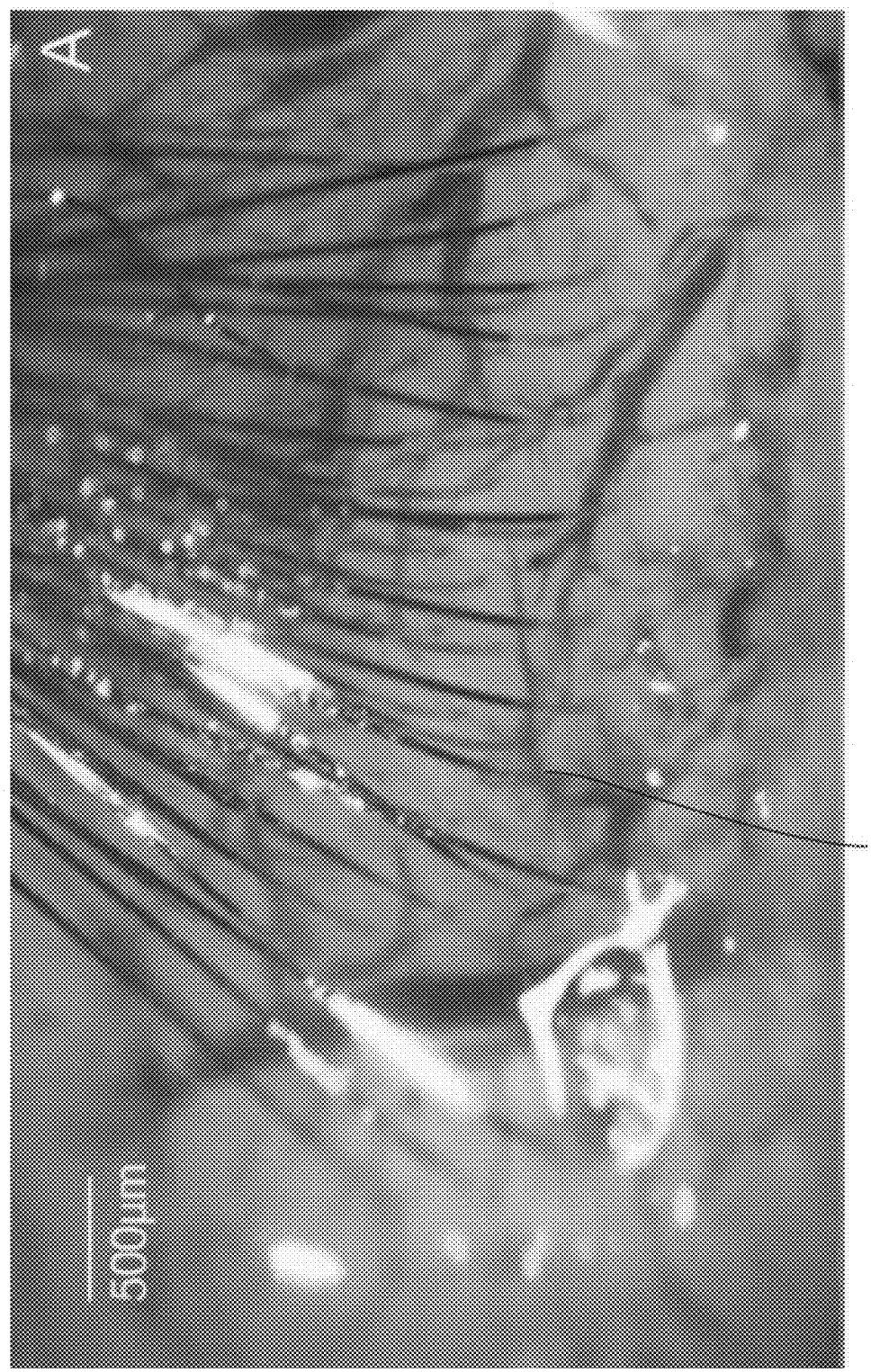
FIG. 9 illustrates an example of electrodes implanted in brain tissue, according to an embodiment.

FIG. 9 illustrates an example of electrodes implanted in brain tissue, according to an embodiment. In a typical example, the disclosed system and methods may implant 96 polymer threads, such as thread 908, into target tissue, each thread with 32 electrodes, for a total of 3,072 electrodes in the array. The electrodes are designed to be, compact, thin, and flexible, with from 5 to 50 μm thread width and nominal thread thickness of 4 to 6 m. In a typical example, the thread length can be approximately 20 mm. The small size and increased flexibility of these probes offers greater biocompatibility, enabling the probes to remain implanted for long periods of time without triggering immune responses. The small thread cross-sectional area can also minimize tissue displacement in the target.

IV. Insertion Verification Components

Figure 10:
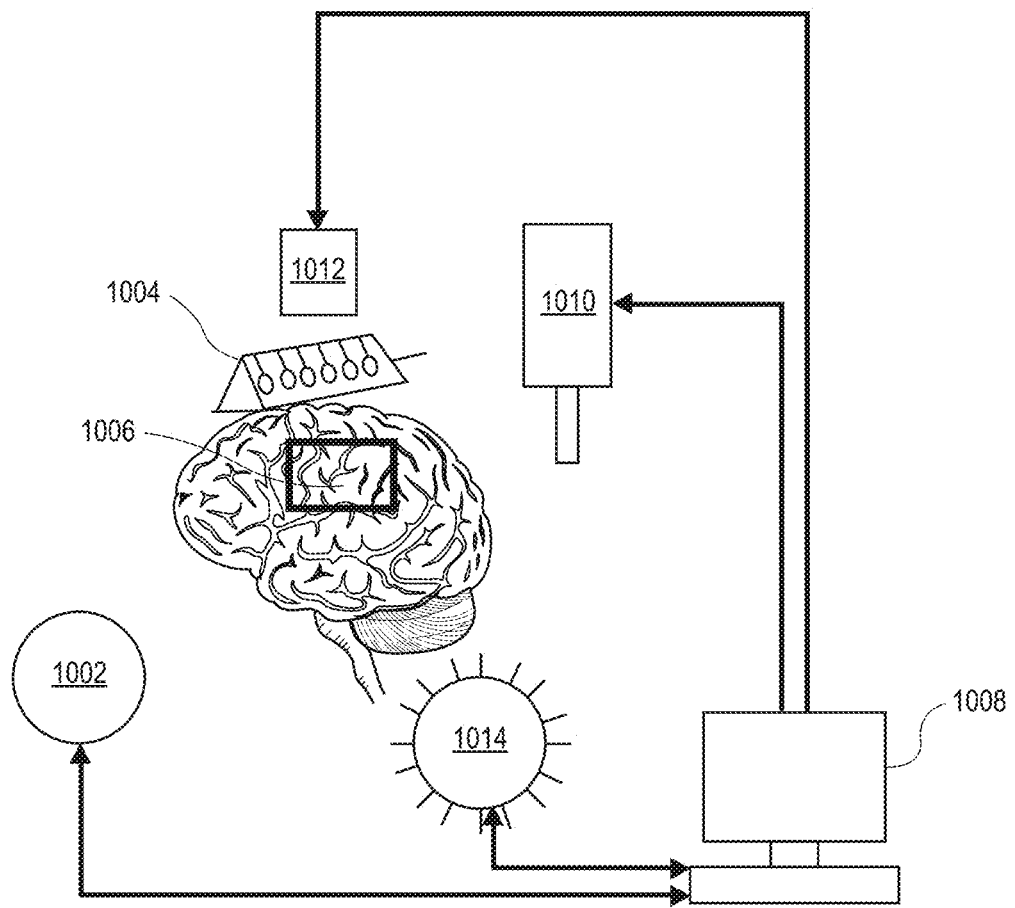
FIG. 10 illustrates example verification components of a system for robotic surgical implantation, according to an embodiment.

FIG. 10 schematically illustrates example verification components of a system for robotic surgical implantation, according to an embodiment. In this example, the verification components may include one or more cameras 1002 that are configured to provide visual verification of implantation of implantable electrode device 1004 in target tissue site 1006. In some embodiments, insertion verification may be performed by components of the inserter head, such as inserter head 200 of the example of FIG. 2. Alternatively, insertion verification may be performed by a separate subsystem, and is not limited by the present disclosure.

The verification components can further include a processing unit, such as computing system 1008, and one or more robotic assemblies, such as robotic assembly 1010 and robotic assembly 1012. Computing system 1008 can process images obtained by cameras 1002 according to a computer vision heuristic in order to determine implantable electrode device 1004 and/or an insertion needle are correctly implanted. Based on this determination, computing system 1008 can send further instructions to robotic assembly 1010 and robotic assembly 1012. For example, computing system 1008 can instruct robotic assemblies 1010 and 1012 to undertake further motions to correct the positioning or implantation of the electrode device. In a second example, computing system 1008 can determine that no further motions are needed, and robotic surgery can proceed to the next stage, e.g. implantation of a subsequent thread, as in the examples of FIGS. 8 and 9.

In some embodiments, the verification components may further include a light source 1008. Light source 1008 may illuminate implantable electrode device 1004 with light of a wavelength selected such that a material associated with implantable electrode device 1004 or its wires appears fluorescent. In particular, verification components such as cameras 1002 can capture light fluoresced by the material in order to generate a three-dimensional map of a plurality of electrodes implanted in target tissue site 1006.

V. Techniques for Robotic Surgical Implantation

Figure 11:
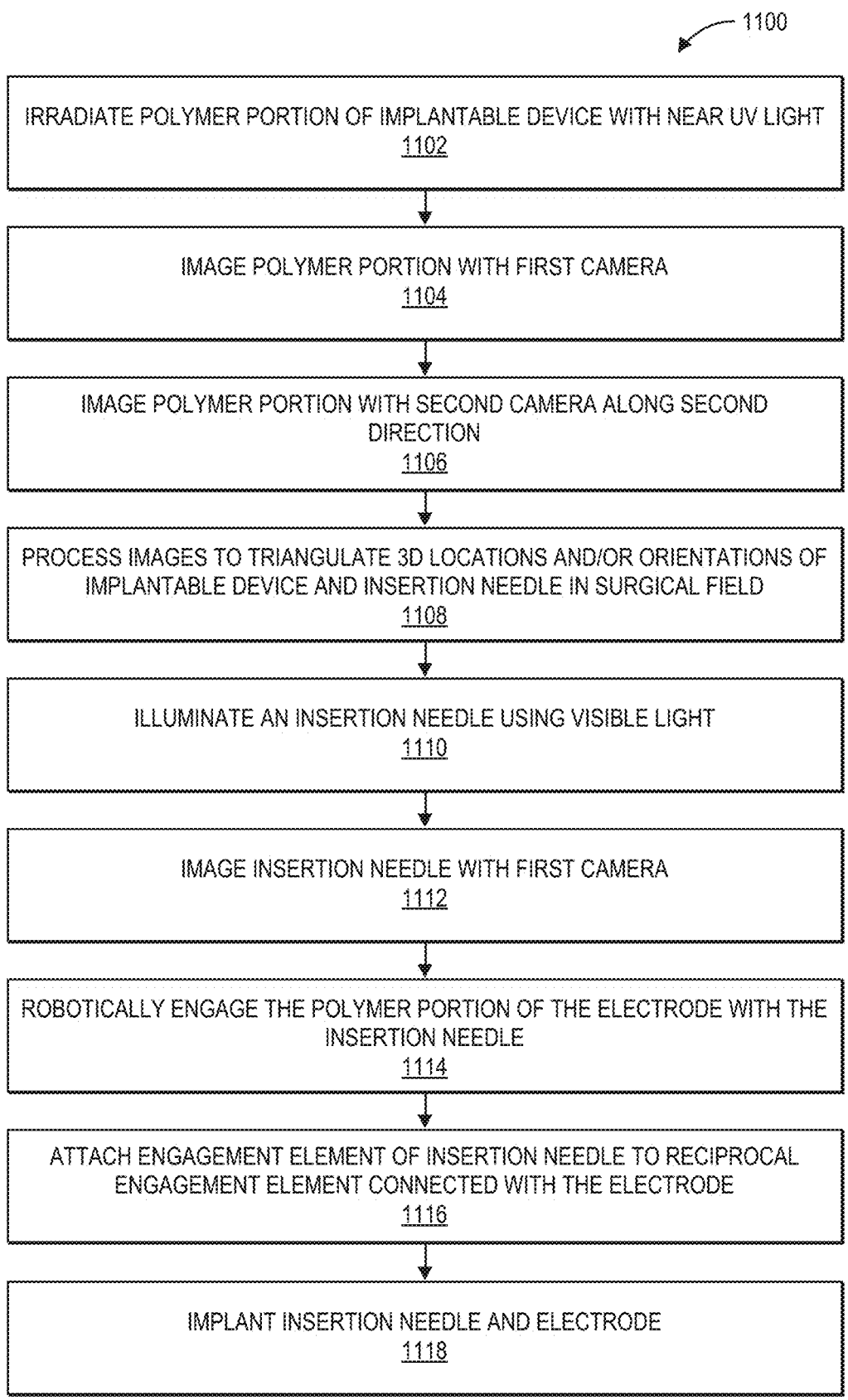
FIG. 11 is a flow chart illustrating an exemplary process for device engagement and robotic surgical implantation, according to an embodiment.

FIG. 11 is a flow chart illustrating an exemplary process 1100 for device engagement and robotic surgical implantation, according to an embodiment. In particular, the disclosed robotic surgery system can be used to implant an electrode device within biological tissue.

In a first step 1102, the robotic surgery system, and/or implantable device engagement components such as those illustrated in FIG. 3, can irradiate a polymer portion of the electrode using a near-ultraviolet (near-UV) wavelength of light. The near-UV radiation can be from a first light source, such as light pipe assembly 306 in FIG. 3. In an embodiment, the first light source can be a first LED or a first laser. The near-UV wavelength can be between 300 nm and 425 nm. In an embodiment, the polymer material is polyimide, and the near-UV wavelength can be chosen in a range that can be absorbed by the polyimide, e.g., wavelengths between 390 nm and 425 nm. The polymer portion may be a reciprocal engagement component of the electrode, such as a polyimide loop, which may fluoresce in response to the irradiation.

In a second step 1104, the robotic surgery system, and/or a first camera such as camera 304 in the example of FIG. 3, may obtain a first image of the polymer portion. The first image may be taken with light fluoresced from the polymer portion in response to the irradiation, as in the example of FIG. 4.

In another embodiment, the light may be absorbed by the polyimide or by other materials in the electrode, insertion needle, or engagement feature. Accordingly, in an embodiment, the images may depict the engagement features as black objects on a white background.

In a third step 1106, the robotic surgery system, and/or a second camera such as camera 302 in the example of FIG. 3, may obtain a second image of the polymer portion along a second direction. The second image may also be taken with light fluoresced from the polymer portion in response to the irradiation, as in the example of FIG. 4. The second camera may be at an angle to the first camera, such as 45° or some other angle, so that the second image may show a different angle of the polymer portion. In an embodiment, the two images can be combined using computer vision techniques to determine location and orientation information, including depth information, about the polymer portion.

In an embodiment, the first camera may be situated substantially perpendicular to a projected edge associated with the electrode (which may be referred to as a "knife's edge"), and the second camera may be situated at an angle relative to the first camera (i.e., the second camera may not be parallel to the first camera). This relative angle may enable the two cameras to obtain depth information. For example, the relative angle may be approximately equal to 45°, or any other angle, and is not limited by the present disclosure. In an embodiment, the may be measured in the plane of the knife's edge and/or the plane of a cartridge housing the electrode device. A first front view camera may be configured to image the engagement features of the plurality of implantable devices arranged on a cartridge in a front view. A second side view camera may be configured to image the engagement features of the plurality of the implantable devices arranged on the cartridge in a side view. The view from the first front view camera may be used to triangulate a general position of the engagement feature along the x-y plane of the surgical field. The view from the second side view camera may be used to triangulate a position of the engagement feature along the z-plane of the surgical field.

In a fourth step 1108, the system and/or a processor can process the first and second images to triangulate a three-dimensional (3D) location of the electrode. The system may use a computer vision heuristic to process the images. In an embodiment, triangulating the location of the electrode further comprises determining, based on the first image and the second image, 3D coordinates of the electrode associated with a motion of the robotic assembly to engage the needle with the implantable device.

In a fifth step 1110, the system and/or a second light source, such as light pipe assembly 306 in FIG. 3, can illuminate an insertion needle using visible light. In an embodiment, the system uses a light source to illuminate the needle with a wavelength of light that does not cause the electrode device to fluoresce. In various embodiments, the visible light can be a specific color, such as red, or can be white light. Using red light can provide a technical advantage by reflecting more strongly and clearly from metal that comprises the needle. In an embodiment, the second light source can be a second LED or a second laser.

Next, in a sixth step 1112, the system and/or the first camera can image the insertion needle. In some embodiments, the second camera can image the insertion needle instead of, or in addition to, the first camera. In an embodiment, the camera images the insertion needle using the visible light reflected by the needle in step 1110.

In a seventh step 1114, the robotic surgery system, and/or implantable device engagement components such as illustrated in FIG. 3, may robotically engage the polymer portion of the electrode with the insertion needle. Based on the images obtained and/or 3D location (e.g., coordinates) determined in operations 1108 and 1112, the system can configure one or more robotic assemblies to engage the needle.

In an eighth step 1116, the robotic surgery system, and/or implantable device engagement components such as illustrated in FIG. 3, may then robotically attach an engagement element of the insertion needle to a reciprocal engagement element connected with the electrode. This may be based on the 3D location and the images taken by the cameras. For example, the system may robotically thread the insertion needle through the polyimide loop on the electrode, in order to remove the electrode from a cartridge, such as cartridge 308 in the example of FIG. 3, in preparation for surgical implantation in the target tissue. In a second example, the system may robotically attach an engagement element (e.g., a loop, a hook, a cup, a protrusion, an extended arm, a "v," etc.) of the electrode to a reciprocal engagement element connected with the insertion needle. Furthermore, a computing system or processing unit may determine details of a robotic assembly's motion and/or send instructions to the robotic assembly. In an exemplary embodiment, configuring the robotic assembly's motion can be further based on coordinates or 3D locations associated with the robotic assembly, and the instructions can configure the motion of the robotic assembly.

In a ninth step 1118, the robotic surgery system and/or the robotic assemblies may then implant the implantable device and/or the needle into the biological tissue. Before implanting the electrode, the robotic surgery system, and/or targeting components such as illustrated in FIG. 2, can determine one or more target tissue sites for implantation. In an embodiment, the robotic surgery system can utilize a computing system, such as computing system 1008 in the example of FIG. 10, or computing system 1500 in the example of FIG. 15A, below, to generate a surgical plan based on the implantation target tissue sites.

Figure 12:
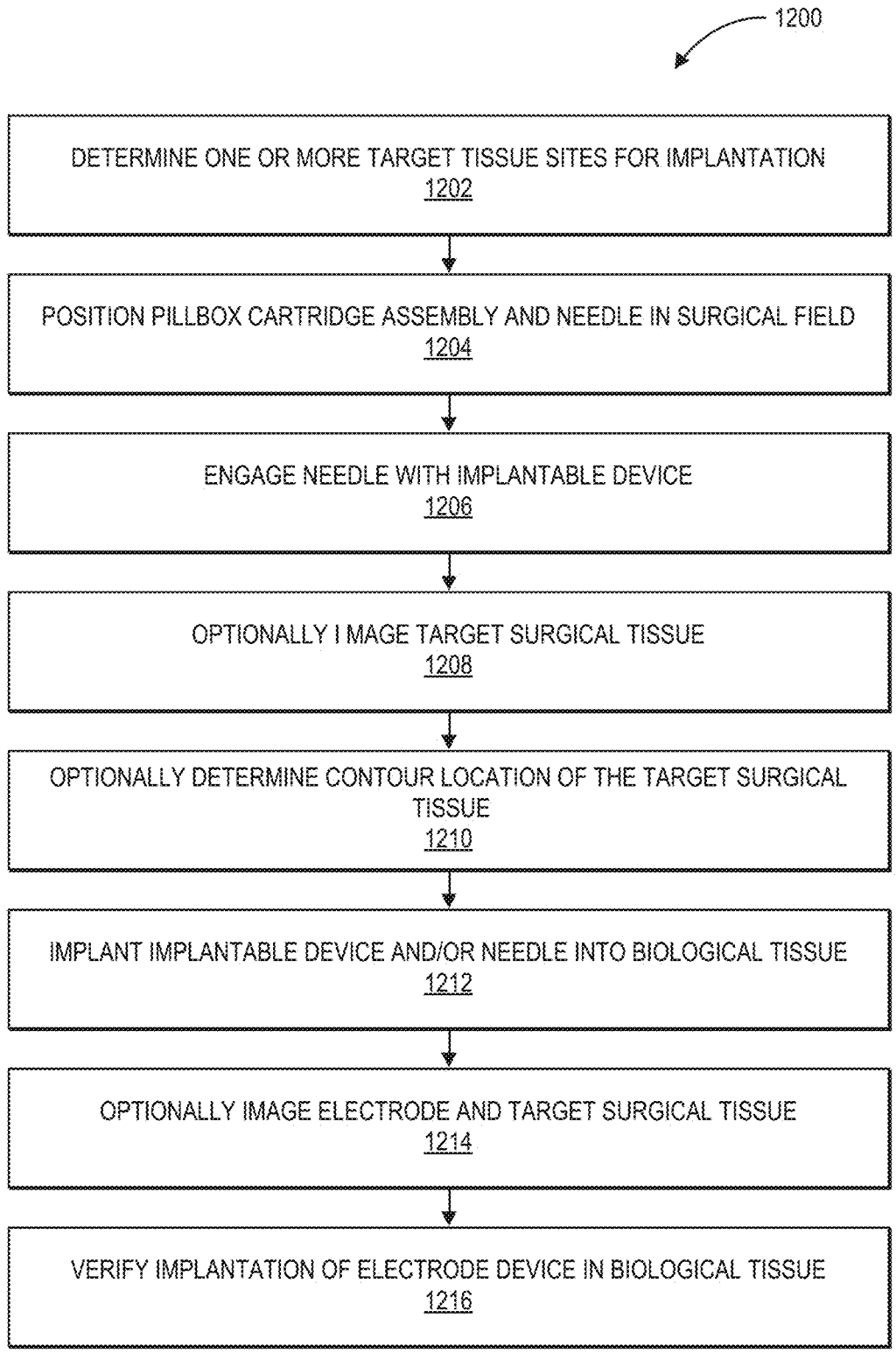
FIG. 12 is a flow chart illustrating an exemplary process for robotic surgical implantation, according to an embodiment.

FIG. 12 is a flow chart illustrating an exemplary process 1200 for robotic surgical implantation, according to an embodiment. In some embodiments, exemplary process 1200 can provide additional detail on implanting the implantable device and/or the needle into the biological tissue in operation 1118 of the example of FIG. 11. In an embodiment, process 1200 may be performed by robotic surgery and/or targeting components, such as those in the examples of FIGS. 1 and 2.

In a first step 1202, the robotic surgery system, and/or targeting components such as illustrated in FIG. 2, can determine one or more target tissue sites for implantation. The robotic surgery system can further utilize a computing system, such as computing system 210 in the example of FIG. 2, to generate a surgical plan based on the implantation targets. The robotic surgery system can use this plan to guide one or more robotic assemblies when implanting the electrode device. In particular, the plan may specify three-dimensional coordinates of motion of one or more robotic assemblies. Such three-dimensional coordinates of motion can be expressed, e.g., in relation to three actuation axes of a respective robotic assembly. In an embodiment, the computing system can use stereoscopic imagery, such as images from different perspectives taken by one or more cameras, in order to determine three-dimensional coordinates of motion applicable to the robotic assemblies.

In an embodiment, the system can image the target surgical tissue, for example, via cameras such as cameras 204 and 205 in the example of FIG. 2 or cameras 1002 in the example of FIG. 10. In an embodiment, one or more of the cameras can be integrated within a microscope, in order to capture microscopic detail of the target site.

In a second step 1204, the robotic surgery system, and/or implantable device engagement components such as illustrated in FIG. 3, may position a pillbox-cartridge assembly and a needle in the surgical field based on the determined targets. In an embodiment, the system and/or a light source can illuminate the electrode with light of a wavelength selected based on a material associated with the electrode device. In an embodiment, the material is polyimide, and the wavelength of the light can be chosen in a range that can be absorbed by the polyimide, e.g., ultraviolet wavelengths between 390 nanometers and 425 nanometers. The system and/or first and second cameras can obtain images of the electrode with light reflected or fluoresced from the material. In another embodiment, the light may be absorbed by the polyamide or by other materials in the electrode, insertion needle, or engagement feature. Accordingly, in an embodiment, the images may depict the engagement features as black objects on a white background.

The system and/or a processor can triangulate, by using a computer vision heuristic to process the first and second images, a location of the electrode. In an embodiment, triangulating the location of the electrode further comprises determining, based on the first image and the second image, three-dimensional coordinates of the electrode associated with a motion of the robotic assembly to engage the needle with the implantable device.

In a third step 1206, the robotic surgery system, and/or implantable device engagement components such as illustrated in FIG. 3, may engage the needle with the implantable device. In an embodiment, the system and/or a camera can image the needle. In an embodiment, when imaging the insertion needle, the system uses a light source to illuminate the needle with another wavelength of light that does not cause the electrode device to fluoresce, such as red light. Based on the images obtained and/or coordinates associated with motion of the robotic assembly determined in operation 1204, the system can configure one or more robotic assemblies to engage the needle. In an exemplary embodiment, a computing system or processing unit may determine details of a robotic assembly's motion and/or send instructions to the robotic assembly.

In an optional sixth step 1208, the robotic surgery system, and/or targeting components such as those illustrated in FIG. 2, may image the target surgical tissue.

In an optional seventh step 1210, the robotic surgery system, and/or targeting components such as those illustrated in FIG. 2, may determine a contour location of the target surgical tissue. For example, the contour location can specify a two-dimensional or three-dimensional surface of the target site, or can specify internal structure of the target tissue, such as neural tissue structure. In various embodiments, the contour location can include a vector drawing, computer-aided design (CAD) drawing, and/or a processed image. In an embodiment, the system can further generate the surgical plan, and/or guide robotic assemblies to implant the electrode surgically, based on the determined tissue contour.

Figure 15A:
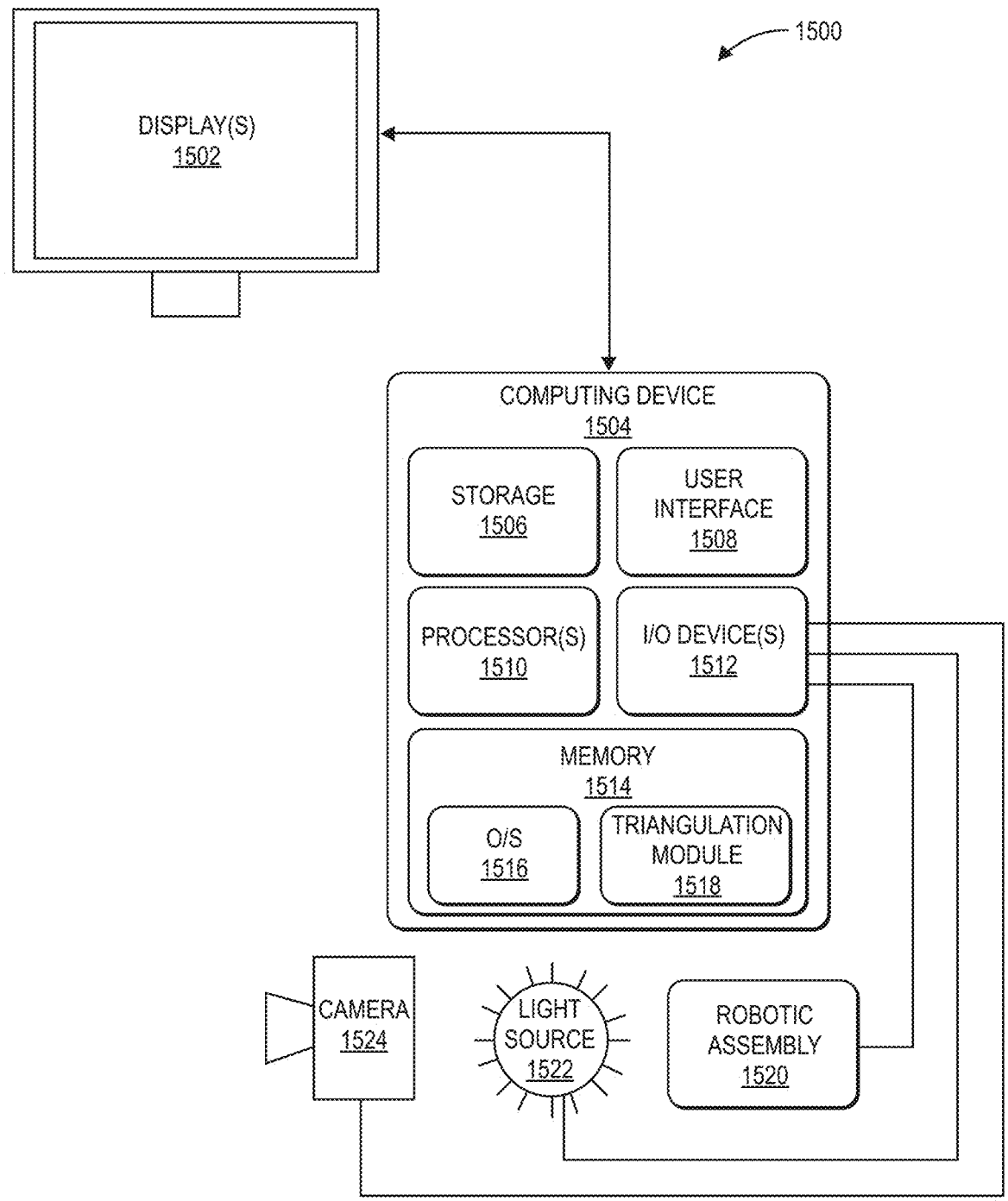
FIG. 15A illustrates an example computing system for robotic surgery guided by computer vision, according to an embodiment.

In an embodiment, a computing system, such as computing system 1008 in the example of FIG. 10 or computing system 1500 in the example of FIG. 15A, can analyze the image from step 1208 to determine the contour location of the tissue. When determining contour locations of the target tissue, the computing system can use a standard filter, such as focus stacking or z-stacking, to determine which parts of an image are in focus. For example, the computing system can use a focused portion of an image at a particular z-stack to determine a height of the target tissue at a particular location, in order to produce a contour map of the tissue. In an embodiment, the computing system can form a composite image (e.g., a stereo composite image) based on target tissue images from multiple cameras (e.g., a left and a right camera), thereby providing Extended Depth of Field (EDF) information. Thus, the computing system can combine multiple images to obtain a composite image, and can generate a surface map based on the composite image. Such a surface map can be used to determine the height or contour of the target tissue at a given location in the composite image. In some embodiments, the system can further use such contour mapping techniques for other purposes, such as insertion verification.

In some embodiments, the system may further use a sensor, such as a "touch-down" sensor, to determine features of a contour of the target tissue. In particular, the system may use computer vision techniques to provide targeting along a plane of a target tissue, while using a touch-down sensor to improve targeting in a dimension perpendicular to the plane imaged with the computer vision.

In a sixth step 1212, the robotic surgery system and/or the robotic assemblies may then implant the implantable device and/or the needle into the biological tissue. The computing system or processing unit can use a surgical plan to guide the one or more robotic assemblies when implanting the electrode device. In particular, the robotic surgery system can use this plan to guide one or more robotic assemblies when implanting the electrode device. In an embodiment, the plan may specify three-dimensional coordinates of motion or target positions of one or more robotic assemblies. Such three-dimensional coordinates of motion can be expressed, e.g., in relation to three actuation axes of a respective robotic assembly. In an embodiment, the computing system can use stereoscopic imagery, such as images from different perspectives taken by one or more cameras, in order to determine three-dimensional coordinates of motion applicable to the robotic assemblies.

Accordingly, the computing system or processing unit can send instructions to the robotic assemblies, such as low-level instructions to undertake specific motions. The robotic assemblies can insert the needle into the target tissue, detach the needle from the electrode device, and remove the needle.

In an optional seventh step 1214, the robotic surgery system, and/or insertion verification components such as those illustrated in FIG. 10, may image the electrode In an eighth step 1216, the robotic surgery system, and/or insertion verification components such as those illustrated in FIG. 10, may verify the implantation of the electrode device into the biological tissue. In an embodiment, the system and/or a camera can obtain an image of the electrode and the target surgical tissue, and can verify implantation of the electrode based on the image. Based on this verification, the computing system can determine whether to end process 1200 or whether further correction is needed. In an embodiment, the computing system can instruct the robotic surgery system and/or the robotic assemblies to return to step 1208 in order to correct the positioning or implantation of the electrode device. In an embodiment, the system may remove the needle only after verifying implantation.

Figure 13:
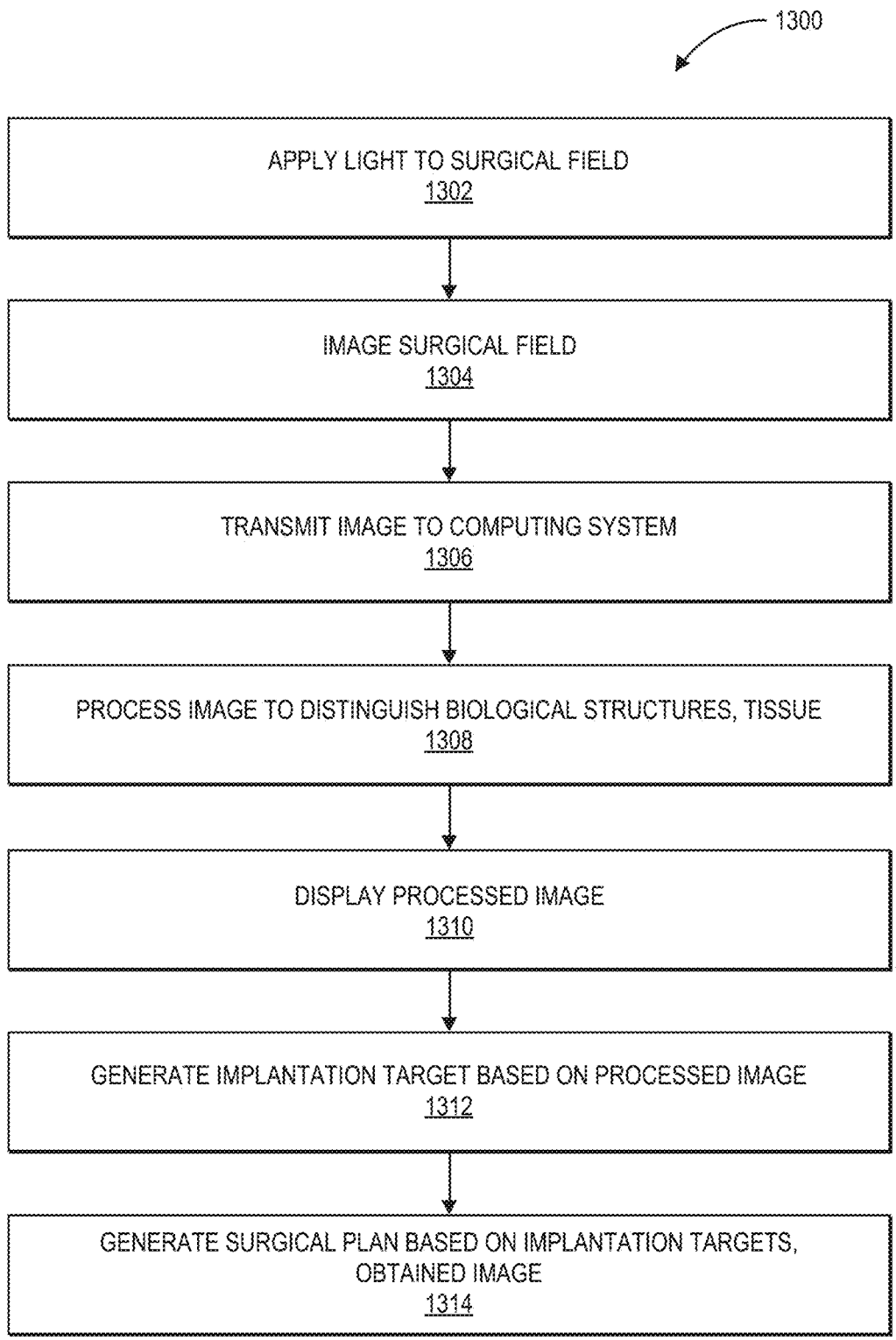
FIG. 13 is a flow chart illustrating an exemplary process for targeting during robotic surgical implantation, according to an embodiment.

FIG. 13 is a flow chart illustrating an exemplary process 1300 for targeting during robotic surgical implantation, according to an embodiment. In some embodiments, exemplary process 1300 can provide additional detail on determining one or more target tissue sites for implantation in operation 1102 of the example of FIG. 11. Exemplary process 1300 may be performed by targeting components, such as targeting system 200 in the example of FIG. 2.

In a first step 1302, a light source may apply a light to a surgical field. In a second step 1304, a camera may image the surgical field. In a third step 1306, the obtained image may be transmitted to a computing system. In a fourth step 1308, the computing system may process the image such that biological structures and biological tissue are distinguishable within the image. The computing system can analyze the image to determine a contour location of the target surgical tissue. In a fifth step 1310, the processed image may be displayed on a user interface of the computing system. In some embodiments, the computing system can apply a computer vision, artificial intelligence, or machine learning heuristic automatically, and does not need to display the image to a user. In a sixth step 1312, the computing system may generate one or more implantation targets based on the processed image. In a seventh step 1314, the computing system may generate a surgical plan based on the implantation targets and/or the obtained image. The robotic surgery system may use this plan to guide one or more robotic assemblies when implanting the electrode device.

Figure 14:
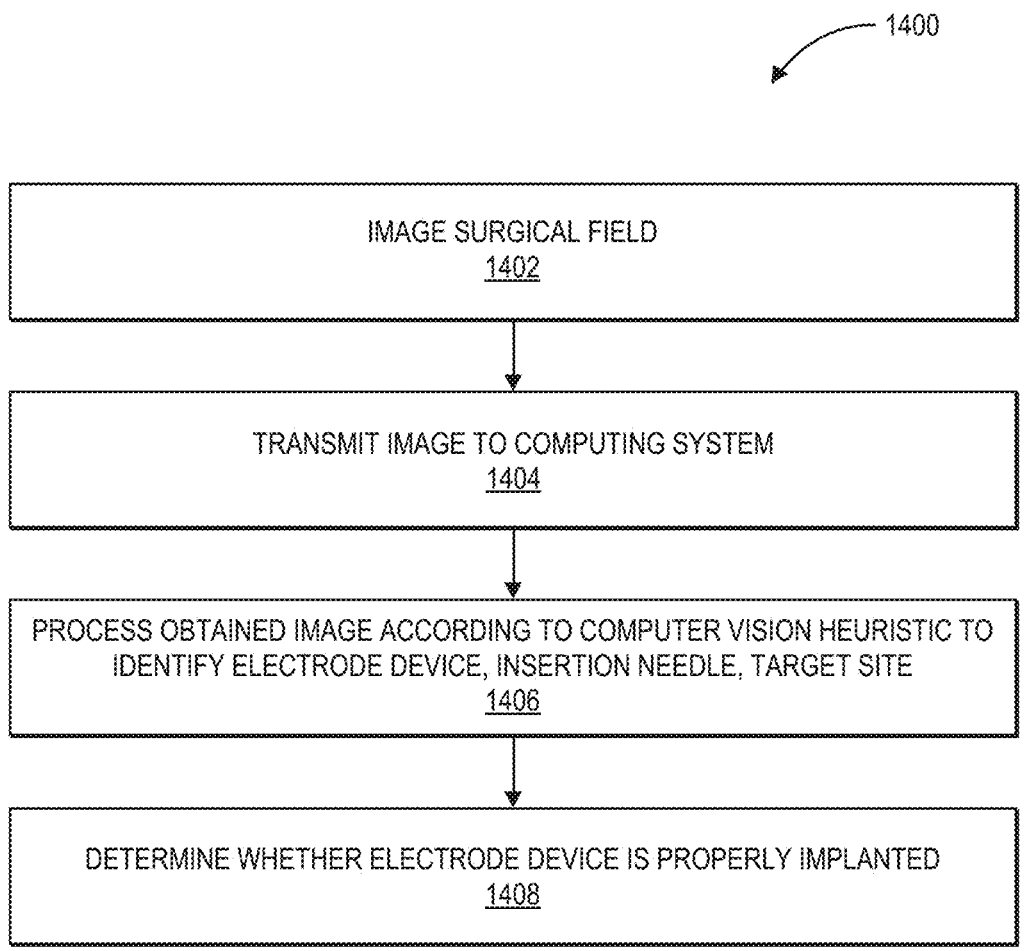
FIG. 14 is a flow chart illustrating an exemplary process for verification during robotic surgical implantation, according to an embodiment.

FIG. 14 is a flow chart illustrating an exemplary process 1400 for verification during robotic surgical implantation, according to an embodiment. In some embodiments, exemplary process 1400 can provide additional detail on verifying the proper implantation of the electrode device into the biological tissue in operation 1110 of the example of FIG. 11. Exemplary process 1400 may be performed by insertion verification components, such as those in the example of FIG. 10, and/or by an inserter head, such as in the example of FIG. 2.

In a first step 1402, a camera is used to image the surgical field. In an embodiment, the camera can image the electrode device with light reflected or fluoresced from a material in the device. In a second step 1404, the obtained image is transmitted to a computing system. In a third step 1406, the obtained image is processed by the computing system according to a computer vision heuristic to identify the electrode device, insertion needle, and/or target site. In a fourth step 1408, the computing system determines whether the electrode device is properly implanted using the processed image. Based on this determination, the robotic surgery system and/or computing system can determine whether further robotic motions are needed to correct the positioning or implantation of the electrode device.

One or more of the images obtained in the processes illustrated in FIGS. 11-14 may be processed using focus stacking techniques (i.e., focal plane merging, z-stacking). In some embodiments, the images of the same surgical field captured at different focal depths (each having different areas of the surgical field in focus) may be combined to form a single image. The focus stacking techniques may be performed at the computing system.

FIG. 15A illustrates components of an example computing system 1500, according at least one example. Computing system 1500 can include one or more display devices such as display devices 1502. The display devices 1502 may be any suitable devices capable of visually presenting information. Examples of such devices may include cathode ray tube (CRT) displays, light-emitting diode (LED) displays, electroluminescent displays (ELD), electronic paper, plasma display panels (PDP), liquid crystal displays (LCD), organic light-emitting diode (OLED) displays, surface-conduction electron-emitter displays (SED), field emission displays (FED), projectors (LCD, CRT, digital light processing (DLP), liquid crystal on silicon (LCoS), LED, hybrid LED, laser diode), and any other suitable device capable of displaying information.

Computing system 1500 may include computing device 1504, which may be connected to the robotic assemblies 1520, light sources 1522, and cameras 1524, as well as to any other devices, such as actuators, etc. The computing device 1504 may be in communication with these devices and/or other components of the robotic surgery system via one or more network(s), wired connections, and the like. The network may include any one or a combination of many different types of networks, such as cable networks, the Internet, wireless networks, cellular networks, radio networks, and other private and/or public networks.

Turning now to the details of the computing device 1504, the computing device 1504 may include at least one memory 1514 and one or more processing units (or processor(s)) 1510. The processor(s) 1510 may be implemented as appropriate in hardware, computer-executable instructions, software, firmware, or combinations thereof. For example, the processor(s) 1510 may include one or more general purpose computers, dedicated microprocessors, or other processing devices capable of communicating electronic information. Examples of the processor(s) 1510 include one or more application-specific integrated circuits (ASICs), field programmable gate arrays (FPGAs), digital signal processors (DSPs) and any other suitable specific or general purpose processors.

Computer-executable instruction, software, or firmware implementations of the processor(s) 1510 may include computer-executable or machine-executable instructions written in any suitable programming language to perform the various functions described. The memory 1514 may include more than one memory and may be distributed throughout the computing device 1504. The memory 1514 may store program instructions (e.g., a triangulation module 1518) that are loadable and executable on the processor(s) 1510, as well as data generated during the execution of these programs. Depending on the configuration and type of memory including the triangulation module 1518, the memory 1514 may be volatile (such as random access memory (RAM)) and/or non-volatile (such as read-only memory (ROM), flash memory, or other memory). In an embodiment, the triangulation module 1518 may receive and/or adjust the linear combination coefficients for Laplacian estimation based on the potentials measured by the CRE. In an embodiment, triangulation module 1518 may implement the linear combination based on these coefficients. The computing device 1504 may also include additional removable and/or non-removable storage 1506 including, but not limited to, magnetic storage, optical disks, and/or tape storage. The disk drives and their associated computer-readable media may provide non-volatile storage of computer-readable instructions, data structures, program modules, and other data for the computing devices. In some implementations, the memory 1514 may include multiple different types of memory, such as static random access memory (SRAM), dynamic random access memory (DRAM), or ROM. The memory 1514 may also include an operating system 1516.

The memory 1514 and the additional storage 1506, both removable and non-removable, are examples of computer-readable storage media. For example, computer-readable storage media may include volatile or non-volatile, removable, or non-removable media implemented in any suitable method or technology for storage of information such as computer-readable instructions, data structures, program modules, or other data. As used herein, modules may refer to programming modules executed by computing systems (e.g., processors) that are part of the triangulation module 1518. The modules of the triangulation module 1518 may include one or more components, modules, and the like. For example, triangulation module 1518 may include modules or components that triangulate the location of objects such as electrodes, insertion needles, and/or target tissue based on computer vision. The computing device 1504 may also include input/output ("I/O") device(s) and/or ports 1512, such as for enabling connection with a keyboard, a mouse, a pen, a voice input device, a touch input device, a display, speakers, a printer, or other I/O device. The I/O device(s) 1512 may enable communication with the other systems of the robotic surgery system.

The computing device 1504 may include a user interface 1508. The user interface 1508 may be utilized by an operator or other authorized user such as the user to access portions of the computing device 1504 (e.g., the triangulation module 1518). In some examples, the user interface 1508 may include a graphical user interface, web-based applications, programmatic interfaces such as application programming interfaces (APIs), or other user interface configurations.

Figure 15B:
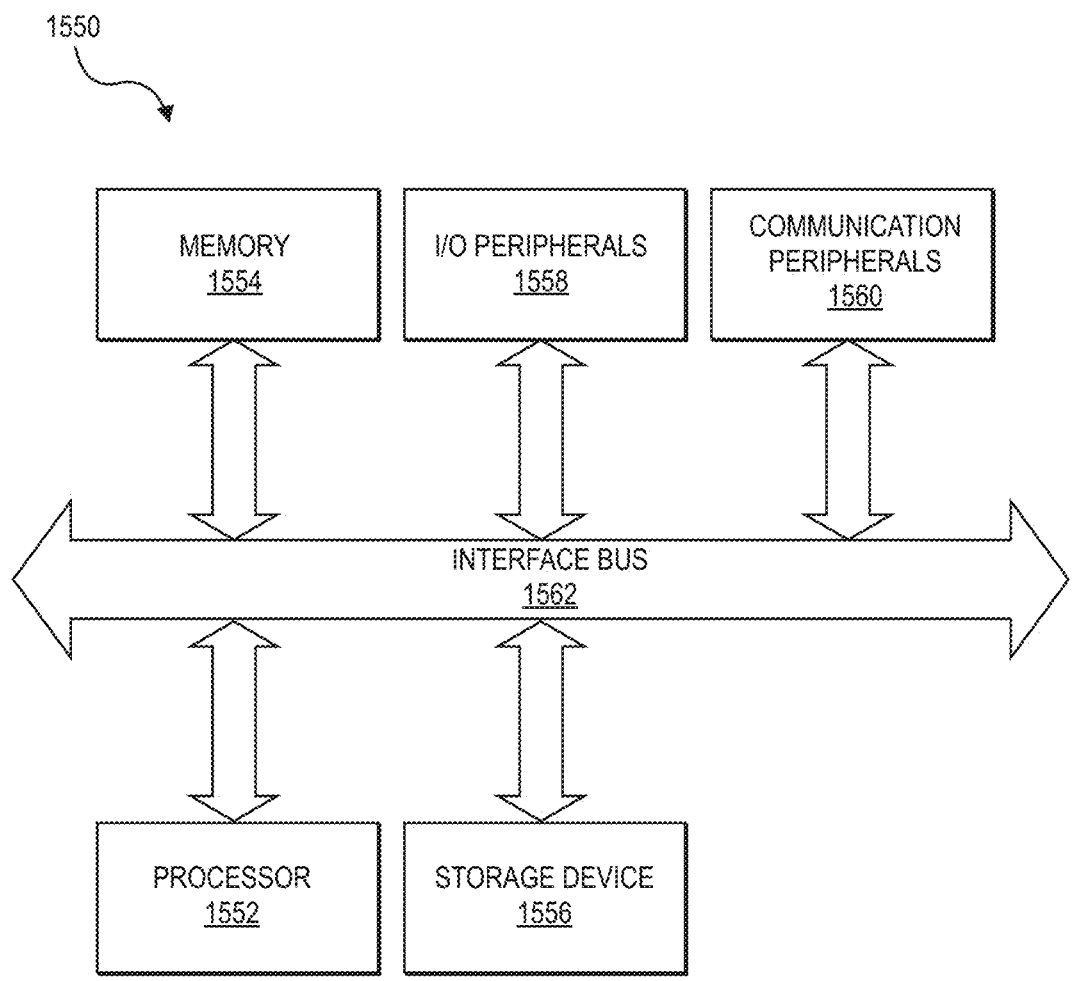
FIG. 15B illustrates example components of a computing system for robotic surgery guided by computer vision, according to an embodiment.

FIG. 15B illustrates examples of components of a computer system 1550, according to at least one example. The computer system 1550 may be a single computer such as a user computing device and/or can represent a distributed computing system such as one or more server computing devices.

The computer system 1550 may include at least a processor 1552, a memory 1554, a storage device 1556, input/output peripherals (I/O) 1558, communication peripherals 1155, and an interface bus 1562. The interface bus 1562 is configured to communicate, transmit, and transfer data, controls, and commands among the various components of the computer system 1550. The memory 1554 and the storage device 1556 include computer-readable storage media, such as Random Access Memory (RAM), Read ROM, electrically erasable programmable read-only memory (EEPROM), hard drives, CD-ROMs, optical storage devices, magnetic storage devices, electronic non-volatile computer storage, for example Flash® memory, and other tangible storage media. Any of such computer-readable storage media can be configured to store instructions or program codes embodying aspects of the disclosure. The memory 1554 and the storage device 1556 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with the computer system 1550.

Further, the memory 1554 includes an operating system, programs, and applications. The processor 1552 is configured to execute the stored instructions and includes, for example, a logical processing unit, a microprocessor, a digital signal processor, and other processors. The memory 1554 and/or the processor 1552 can be virtualized and can be hosted within another computing system of, for example, a cloud network or a data center. The I/O peripherals 1558 include user interfaces, such as a keyboard, screen (e.g., a touch screen), microphone, speaker, other input/output devices, and computing components, such as graphical processing units, serial ports, parallel ports, universal serial buses, and other input/output peripherals. The I/O peripherals 1558 are connected to the processor 1552 through any of the ports coupled to the interface bus 1562. The communication peripherals 1155 are configured to facilitate communication between the computer system 1550 and other computing devices over a communications network and include, for example, a network interface controller, modem, wireless and wired interface cards, antenna, and other communication peripherals.

The terms "computing system" and "processing unit" as used herein are intended for all purposes to be interpreted broadly and is defined for all uses, all devices, and/or all systems and/or systems in this disclosure as a device comprising at least a central processing unit, a communications device for interfacing with a data network, transitory computer-readable memory, and/or a non-transitory computer-readable memory and/or media. The central processing unit carries out the instructions of one or more computer programs stored in the non-transitory computer-readable memory and/or media by performing arithmetical, logical, and input/output operations to accomplish in whole or in part one or more steps of any method described herein. A computing system is usable by one or more users, other computing systems directly and/or indirectly, actively and/or passively for one or more suitable functions herein. The computing system may be embodied as computer, a laptop, a tablet computer, a smartphone, and/or any other suitable device and may also be a networked computing system, a server, or the like. Where beneficial, a computing system can include one or more human input devices such as a computer mouse and/or keyboard and one or more human interaction device such as one or more monitors. A computing system may refer to any input, output, and/or calculating device associated with providing an experience to one or more users. Although one computing system may be shown and/or described, multiple computing systems may be used. Conversely, where multiple computing systems are shown and/or described, a single computing device may be used.

The computer vision based techniques for robotic surgery may be used for various applications including, for example, neurosurgery. In some embodiments, a plurality of implantable devices may be inserted or implanted in sequence using the techniques described herein.

In some embodiments, the implantable device may be configured for implantation in biological tissue. Biological tissue may include, but is not limited to, the brain, muscle, liver, pancreas, spleen, kidney, bladder, intestine, heart, stomach, skin, colon, etc. Additionally, the implantable device may be used in connection with any suitable multi-cellular organism including, but not limited to, invertebrates, vertebrates, fish, bird, mammals, rodents (e.g., mice, rats), ungulates, cows, sheep, pigs, horses, non-human primates, and humans. Moreover, biological tissue may be ex vivo (e.g., tissue explant), or in vivo (e.g., the method is a surgical procedure performed on a patient).

While illustrative embodiments have been described herein, the scope thereof includes any and all embodiments having equivalent elements, modifications, omissions, combinations (e.g., of aspects across various embodiments), adaptations and/or alterations as would be appreciated by those in the art based on the present disclosure. For example, the number and orientation of components shown in the exemplary systems may be modified.

Thus, the foregoing description has been presented for purposes of illustration. It is not exhaustive and is not limiting to the precise forms or embodiments disclosed. Modifications and adaptations will be apparent to those skilled in the art from consideration of the specification and practice of the disclosed embodiments.

What is claimed is:

1. A method for robotic surgical implantation of an electrode, the method comprising:
   irradiating, by a first light source, a polymer portion of the electrode using a near-ultraviolet (near-UV) wavelength of light, wherein the near-UV wavelength is between 300 nanometers and 425 nanometers, the irradiating to cause the polymer portion of the electrode to fluoresce;
   obtaining, by a first camera, a first image of the polymer portion fluorescing;
   obtaining, by a second camera, a second image of the polymer portion fluorescing;
   triangulating, by a processor, a three-dimensional (3D) location of the electrode based on the first and second images;
   illuminating, by a second light source, an insertion needle using visible light;
   obtaining, by the first camera, a third image of the insertion needle illuminated by the visible light;
   analyzing, by the processor, the 3D location and the third image to determine instructions for motion of a robotic assembly to robotically engage the polymer portion of the electrode with the insertion needle;
   threading, by the robotic assembly according to the instructions received from the processor, the insertion needle through a reciprocal engagement element of the polymer portion of the electrode, wherein the reciprocal engagement element comprises a loop, and wherein threading the insertion needle through the reciprocal engagement element further comprises threading an engagement element of the insertion needle through the loop; and
   surgically implanting the electrode using the insertion needle.

2. The method of claim 1, wherein the insertion needle comprises metal and the visible light is red light.

3. The method of claim 1, wherein the polymer portion comprises polyimide, wherein the near-UV wavelength of the light is between 390 nanometers and 425 nanometers, and wherein the light fluoresced from the polymer portion comprises green light.

4. The method of claim 1, wherein the first camera is situated substantially perpendicular to a planar surface of a projected edge associated with the electrode, and wherein the second camera is situated at an angle greater than 5° relative to the first camera.

5. The method of claim 1, further comprising:
   obtaining a fourth image of a target surgical tissue; and
   determining, based on the fourth image, a contour location of the target surgical tissue;
   wherein surgically implanting the electrode is further based on the determined contour location.

6. The method of claim 5, wherein surgically implanting the electrode further comprises:
   obtaining a fifth image of the electrode and the target surgical tissue; and
   verifying, based on the fifth image, an implantation of the electrode.

7. A system for robotic surgical implantation of an electrode, comprising:
   a first light source configured to irradiate a polymer portion of the electrode using a near-ultraviolet (near-UV) wavelength of light, and wherein the near-UV wavelength is between 300 nanometers and 425 nanometers, the irradiating to cause the polymer portion of the electrode to fluoresce;
   a second light source configured to illuminate an insertion needle using visible light;
   a first camera configured to obtain a first image of the polymer portion fluorescing, the first camera further configured to obtain a third image of the insertion needle illuminated by the visible light;
   a second camera configured to obtain a second image of the polymer portion fluorescing;
   a processor configured to triangulate a three-dimensional (3D) location of the electrode based on the first and second images and analyze the 3D location and the third image to determine instructions for motion of a robotic assembly to robotically engage the polymer portion of the electrode with the insertion needle;
   the robotic assembly configured to engage a reciprocal engagement element of the polymer portion of the electrode with the insertion needle according to the instructions received from the processor wherein the reciprocal engagement element comprises a loop, and wherein threading the insertion needle through the reciprocal engagement element further comprises threading an engagement element of the insertion needle through the loop; and
   the robotic assembly is further configured to surgically implant the electrode.

8. The system of claim 7, wherein the insertion needle comprises metal and the visible light is red light.

9. The system of claim 7, wherein:
   the first camera or the second camera is further configured to obtain a fourth image of a target surgical tissue;
   the processor is further configured to determine, based on the fourth image, a contour location of the target surgical tissue; and
   the robotic assembly is further configured to surgically implant the electrode based on the determined contour location.

10. A method for robotic surgical implantation of an electrode, the method comprising:

providing a micro-manufactured bio-compatible electrode having a polymer engagement portion;

irradiating the polymer engagement portion of the electrode using near-ultraviolet (near-UV) light in order to cause the polymer engagement portion to fluoresce;

imaging fluorescence of the polymer engagement portion by first and second cameras during the irradiating;

triangulating, by a processor, a three-dimensional (3D) location of the electrode based on the imaging;

illuminating a metal insertion needle with visible light;

analyzing, by the processor, the 3D location with respect to the illuminated metal insertion needle to determine instructions for robotically engaging the polymer engagement portion of the electrode with the metal insertion needle, wherein the polymer engagement portion comprises a loop, and wherein engaging the metal insertion needle with the polymer engagement portion comprises threading the metal insertion needle through the loop;

guiding, by a robotic assembly according to the instructions from the processor, the metal insertion needle to engage the polymer engagement portion;

driving the metal insertion needle with the engaged polymer engagement portion to a position near target tissue;

inserting the metal insertion needle with the engaged polymer engagement portion into the target tissue; and retracting the metal insertion needle, leaving the electrode implanted in the target tissue.

11. The method of claim 10 wherein the visible light is colored red.

12. The method of claim 10, wherein the polymer engagement portion comprises polyimide, wherein the near-UV light has a wavelength between 390 nanometers and 425 nanometers, and wherein the light fluoresced from the polymer engagement portion comprises green light.

13. The method of claim 10, wherein the first camera is situated substantially perpendicular to a planar surface of a projected edge associated with the electrode, and wherein the second camera is situated at an angle greater than 5° relative to the first camera.

14. The method of claim 10 further comprising:

shining green light on the target tissue in order to provide contrast for viewing blood vessels, wherein the inserting is directed to avoid blood vessels in the target tissue.

\* \* \* \* \*